US012653467B2

(12) United States Patent
Rogers et al.

(10) Patent No.: US 12,653,467 B2
(45) Date of Patent: Jun. 16, 2026

(54) FLAT EMITTER WITH COMPLIANT SUPPORTED END

(71) Applicant: GE Precision Healthcare LLC, Waukesha, WI (US)

(72) Inventors: Carey Rogers, Waukesha, WI (US); Kevin Kruse, Muskego, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 129 days.

(21) Appl. No.: 18/608,670

(22) Filed: Mar. 18, 2024

(65) Prior Publication Data

US 2025/0292986 A1 Sep. 18, 2025

(51) Int. Cl.
| | |
|---|---|
| *H01J 35/06* | (2006.01) |
| *A61B 6/03* | (2006.01) |
| *A61B 6/40* | (2024.01) |
| *H01J 1/18* | (2006.01) |
| *H01J 1/94* | (2006.01) |

(52) U.S. Cl.
CPC ................ *A61B 6/032* (2013.01); *A61B 6/40* (2013.01); *H01J 1/18* (2013.01); *H01J 1/94* (2013.01); *H01J 35/064* (2019.05); *H01J 2235/06* (2013.01)

(58) Field of Classification Search
CPC .......... H01J 35/066; H01J 35/064; H01J 1/94; H01J 2235/06; H01J 35/06
See application file for complete search history.

(56) References Cited

U.S. PATENT DOCUMENTS

| | | | |
|---|---|---|---|
| 6,259,193 B1 * | 7/2001 | Lipkin ...................... | H01J 1/18 |
| | | | 313/271 |
| 7,693,265 B2 | 4/2010 | Hauttmann et al. | |
| 8,294,350 B2 | 10/2012 | Freudenberger et al. | |
| 8,401,151 B2 | 3/2013 | Frontera et al. | |
| 8,548,124 B2 * | 10/2013 | Hauttmann ............. | H01J 35/14 |
| | | | 378/143 |
| 9,251,987 B2 | 2/2016 | Zhang et al. | |
| 9,711,320 B2 | 7/2017 | Zou et al. | |
| 10,109,450 B2 | 10/2018 | Virshup et al. | |
| 10,636,608 B2 | 4/2020 | Lampe et al. | |
| 11,515,117 B2 * | 11/2022 | Cross .................... | H01J 35/064 |

(Continued)

FOREIGN PATENT DOCUMENTS

| | | |
|---|---|---|
| DE | 102010020151 A1 | 11/2011 |
| DE | 102010039765 A1 | 3/2012 |

(Continued)

OTHER PUBLICATIONS

EP application 25159507.0 filed Feb. 21, 2025—partial Search Report issued Nov. 11, 2025; 14 pages.

(Continued)

*Primary Examiner* — Uzma Alam
*Assistant Examiner* — Mamadou Faye
(74) *Attorney, Agent, or Firm* — McCoy Russell LLP

(57) ABSTRACT

Various methods and systems are provided for an emitter assembly for a cathode of an X-ray tube. In one example, an emitter assembly comprises a first end of a substantially flat emitter supported by two rods extending from a two-rod insulator assembly, and a second end of the substantially flat emitter supported by a compliant, single rod insulator assembly.

20 Claims, 13 Drawing Sheets

(56) References Cited

U.S. PATENT DOCUMENTS

| | | | |
|---|---|---|---|
| 2007/0246789 A1 | 10/2007 | Freudenberger et al. | |
| 2010/0067663 A1* | 3/2010 | Freudenberger | H01J 1/16 |
| | | | 378/136 |
| 2011/0280377 A1 | 11/2011 | Freudenberger et al. | |
| 2014/0079187 A1* | 3/2014 | Zhang | H01J 1/16 |
| | | | 313/341 |
| 2018/0350549 A1* | 12/2018 | Lampe | H01J 35/025 |
| 2020/0066475 A1* | 2/2020 | Steinlage | H01J 1/14 |

FOREIGN PATENT DOCUMENTS

| | | |
|---|---|---|
| DE | 201210205715 A1 | 10/2013 |
| EP | 3063780 B1 | 6/2021 |
| JP | 2014232629 A | 12/2014 |

OTHER PUBLICATIONS

JP2014232629 English Abstract; Espacenet.com Feb. 11, 2026; 1 page.

* cited by examiner

300

344     354     364

362     368     342

358

356     352     366

360     348

372

374

370

376     380

350

378

301 z x     y

366

346

1202

1204

1206    1208

301

Y

Z    X

FLAT EMITTER WITH COMPLIANT SUPPORTED END

FIELD

Embodiments of the subject matter disclosed herein relate to an emitter of a cathode for imaging systems, for example, X-ray imaging systems.

BACKGROUND

In an X-ray tube, ionizing radiation is created by accelerating electrons in a vacuum from a cathode to an anode via an electric field. The electrons originate from an emitter of the cathode with current flowing therethrough. The emitter may be heated by a current flowing through it to liberate electrons from the cathode and accelerate the electrons toward the anode. Additionally, electrodes at different voltages may be placed around the emitter to focus the electron beam towards the anode, and to influence the size and position of the X-ray emitting spot. The cathode may be configured with additional focusing elements, such as a focusing architecture, for example, to further influence the size and position of the X-ray emitting spot.

BRIEF DESCRIPTION

In one embodiment, a substantially flat emitter of a cathode comprises a first end of an emitter supported by two rods extending from a two-rod insulator assembly; and a second end of the emitter supported by a compliant, single rod insulator assembly.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
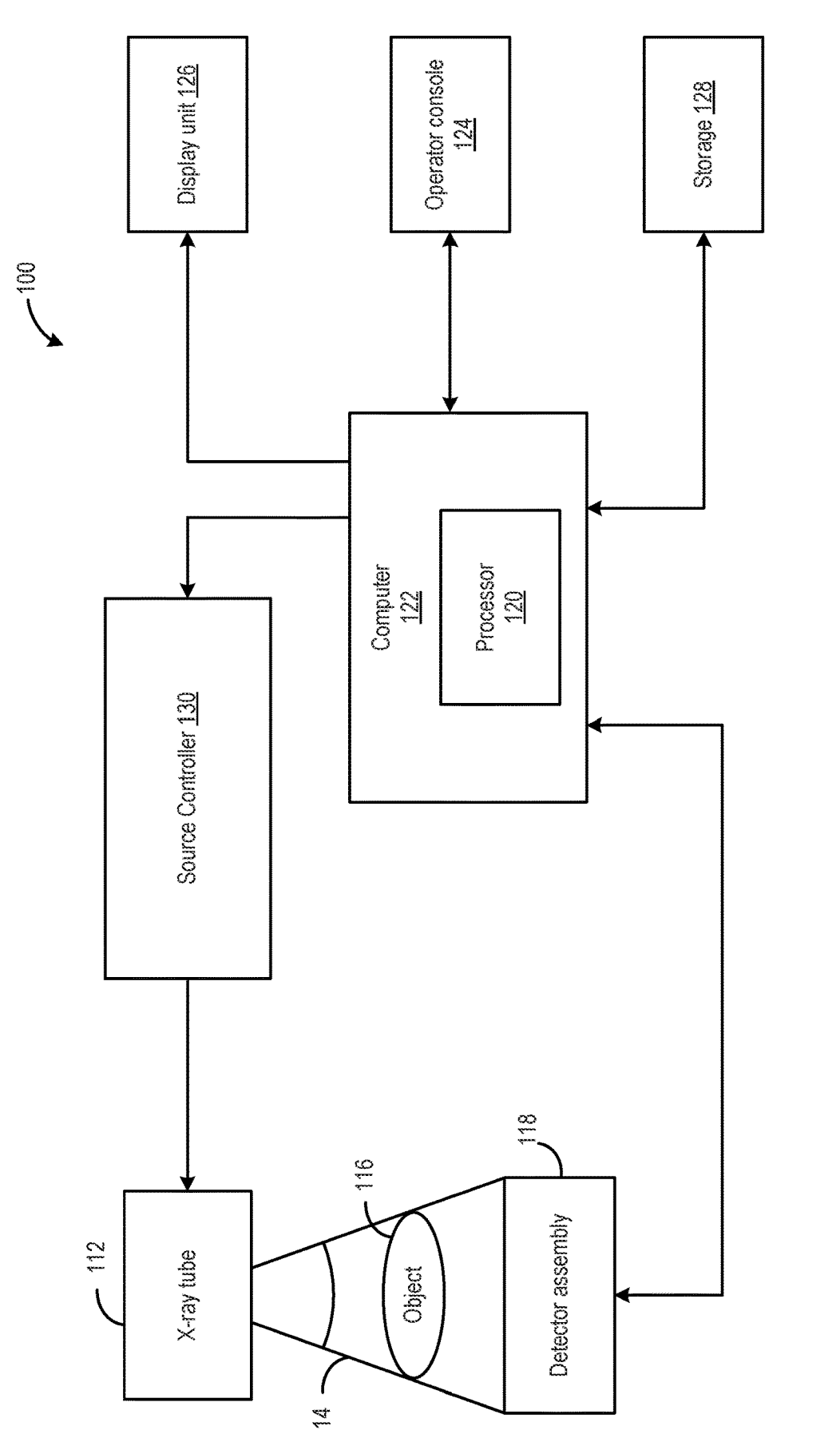
FIG. 1 shows a block diagram of an example of an imaging system.
Figure 2:
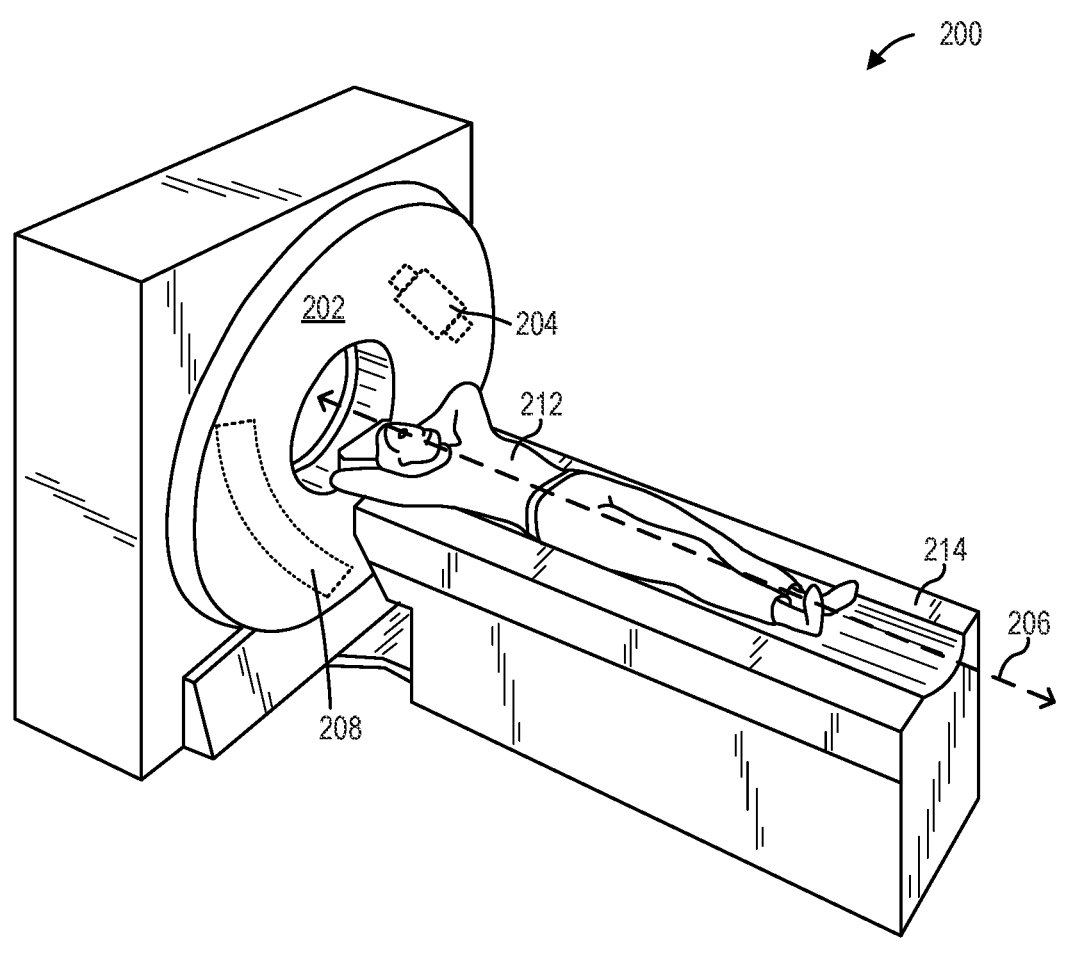
FIG. 2 shows a pictorial view of an imaging system, which may be an embodiment of the imaging system of FIG. 1, according to an embodiment.
Figure 3:
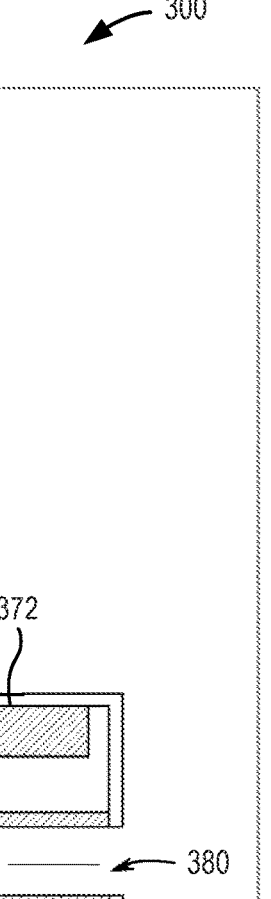
FIG. 3 shows a schematic of a cross-sectional view of a portion of an X-ray tube which may be included in the imaging system of FIG. 1 and/or FIG. 2.
Figure 6:
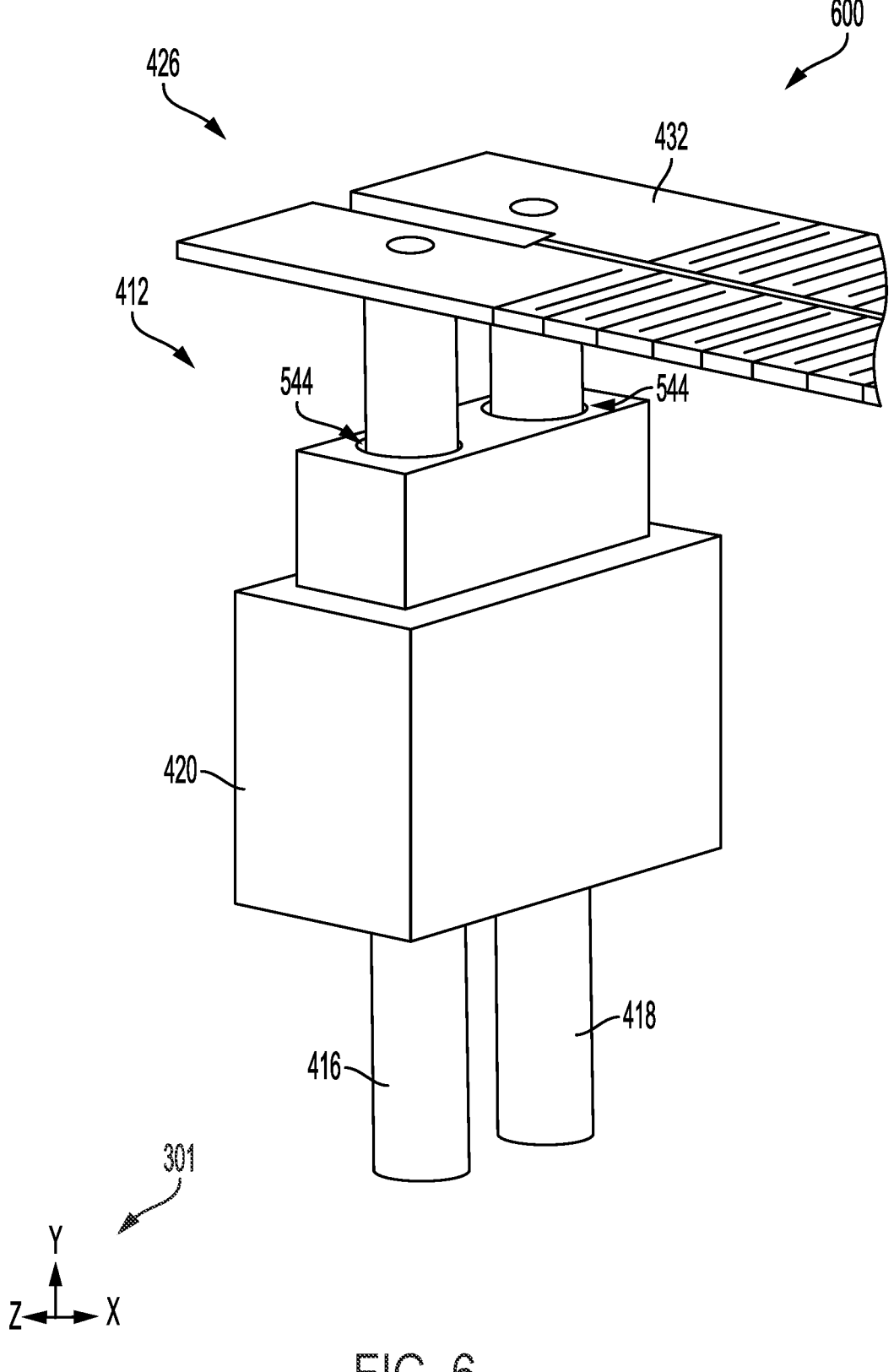
FIG. 6 shows a perspective view of a two-rod insulator assembly of the first example X-ray emitter assembly of FIG. 5.
Figure 7:
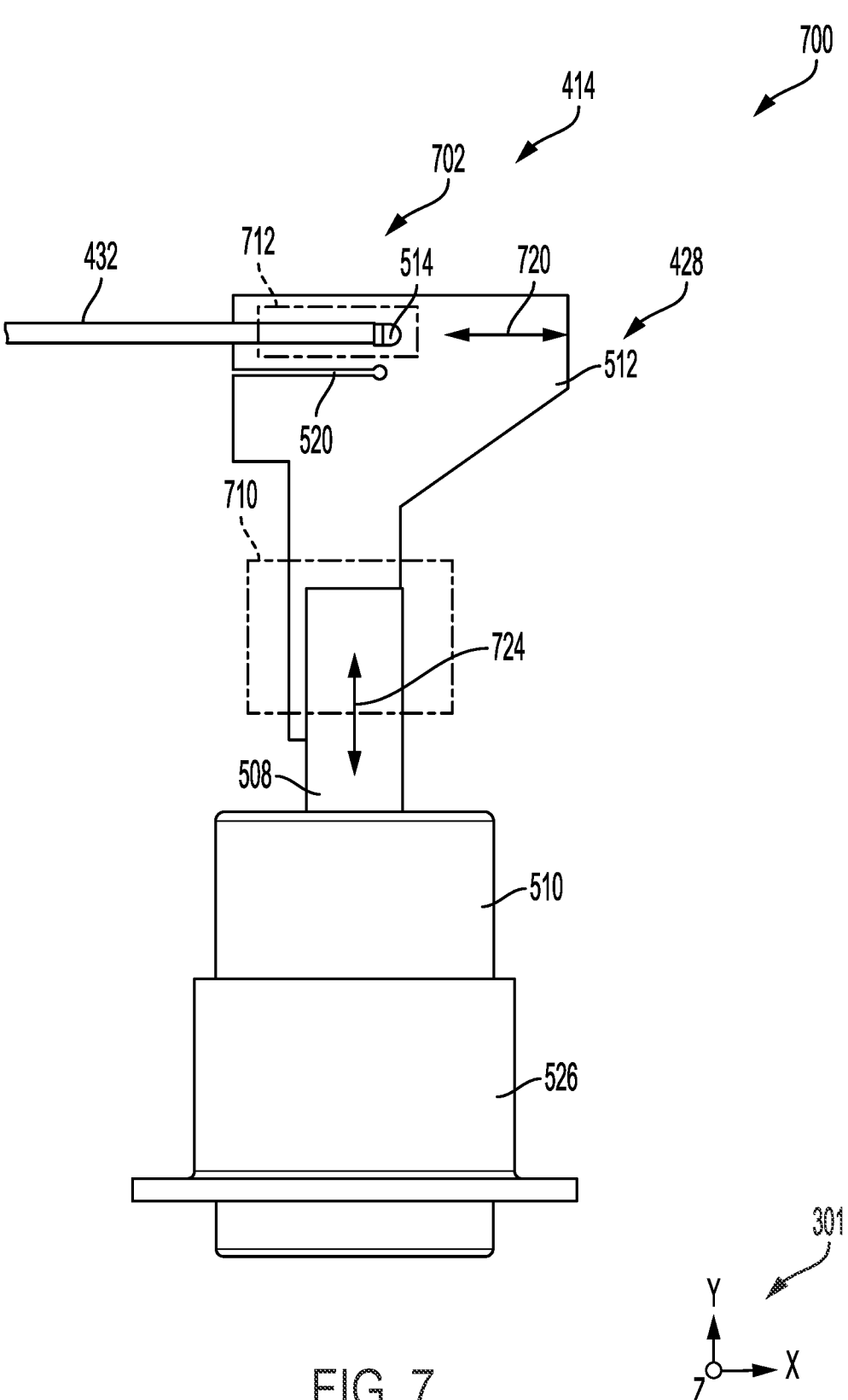
FIG. 7 shows a side view of a compliant, single rod insulator assembly of the first example X-ray emitter assembly of FIG. 5.
Figure 8:
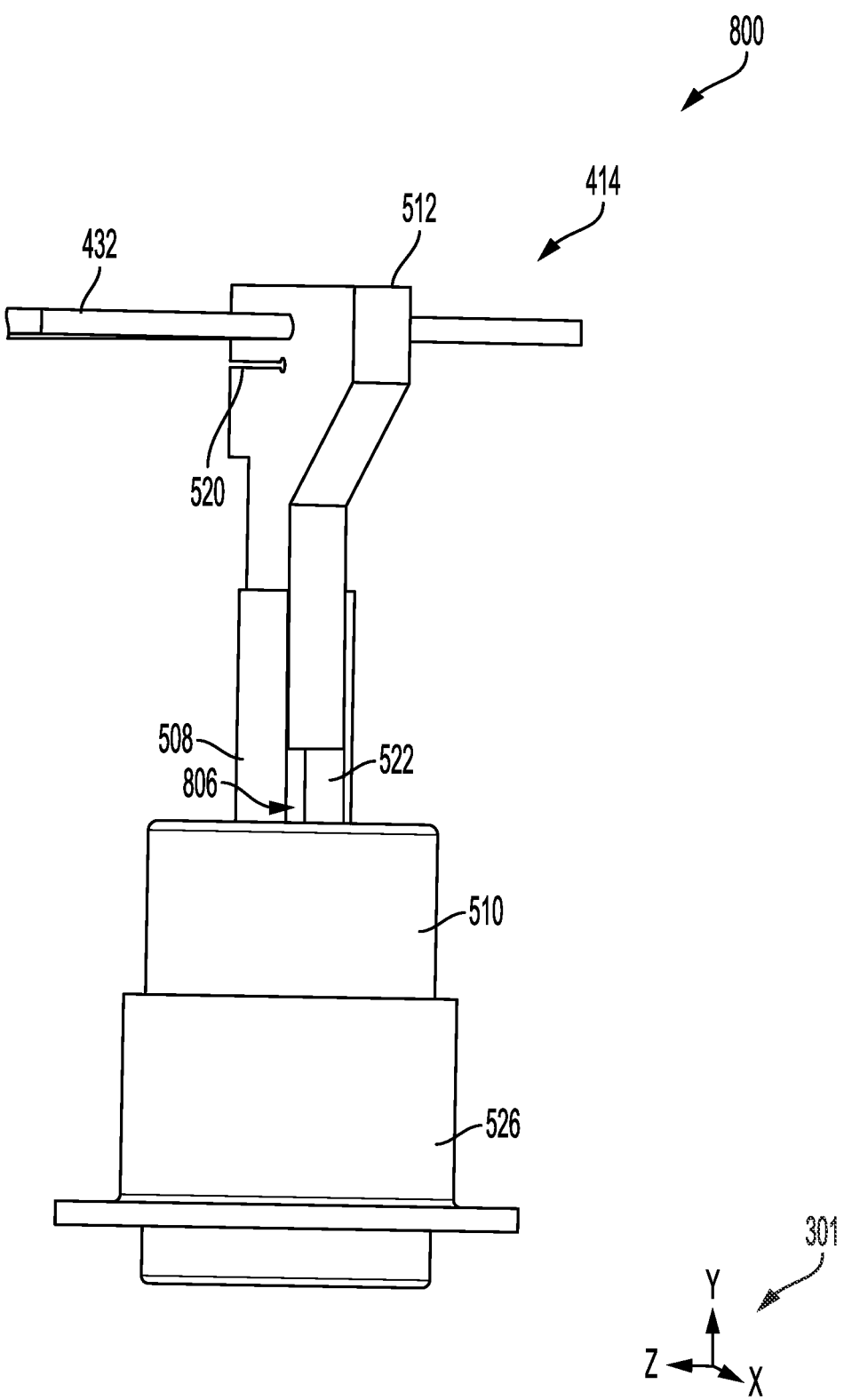
FIG. 8 shows a perspective view of the compliant, single rod insulator assembly of FIG. 7.
Figure 9:
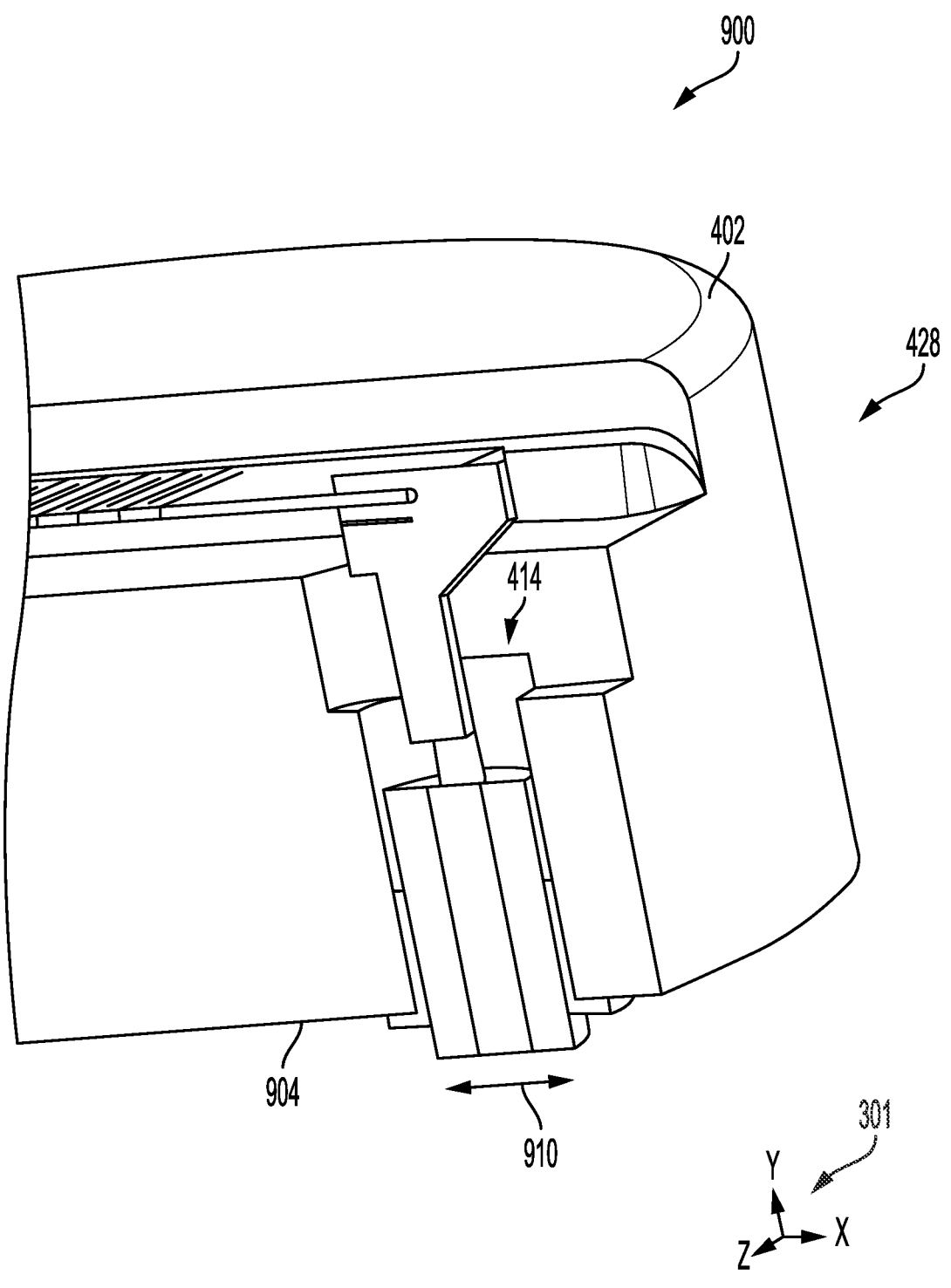
FIG. 9 shows a perspective view of the cathode of FIG. 4, including the compliant, single rod insulator assembly of the first example X-ray emitter assembly.

The following description relates to various embodiments for an emitter of a cathode of an X-ray tube. The X-ray tube may be included in an X-ray imaging system, an example of which is shown in FIG. 1. The X-ray imaging system may be an interventional radiography imaging system, a fluoroscopic imaging system, a mammography imaging system, a fixed or mobile radiography (RAD) imaging system, a tomographic imaging system, a computed tomography (CT) imaging system, and so on. FIG. 2 shows a pictorial view of an imaging system, such as the X-ray imaging system of FIG. 1. The X-ray imaging system includes an X-ray source (e.g., an X-ray tube) to generate irradiating X-ray beams. A cross-sectional schematic view of an X-ray tube is shown in FIG. 3. The X-ray tube of FIG. 3 includes an anode assembly and a cathode assembly, the latter of which includes a cathode, as is shown in further detail in FIG. 4. The cathode assembly includes an emitter mounted in a cathode cup. A first example X-ray emitter assembly is shown in a perspective view in FIG. 5, where an emitter is a substantially flat emitter supported at a first end by two rods extending from a two-rod insulator assembly, and supported at a second end of the emitter by a compliant, single rod insulator assembly. Compliant, as used herein, defines a flexible element, mechanism, or assembly that achieves force and motion transmission through elastic body deformation. The compliant, single rod insulator assembly of the first example X-ray emitter assembly includes a substantially flat support plate comprising a socket, where the emitter is inserted into the socket and the substantially flat support plate is perpendicular to the emitter. At the first end, the emitter is fixedly coupled to the two rods, for example, via welding or brazing. In this way, the emitted is rigidly positioned at the first end. At the second end, the emitter is held by the compliant, single rod insulator assembly such that the emitter may expand in a lengthwise direction and/or a lateral direction. The compliant, single rod insulator assembly provides accommodation for thermal and mechanical expansion of the emitter without placing a large retraining force on the emitter that may cause deformation. A heating current is supplied to the emitter via the two-rod insulator assembly. Current is conducted into the emitter through a first rod of the two rods, into and through the emitter thus heating up the emitter, and out of the emitter through a second rod of the two rods. FIG. 6 shows a detailed view of the two-rod insulator assembly, and FIGS. 7-9 show detailed views of the compliant, single rod insulator assembly. A second example X-ray emitter assembly is shown in a perspective views in FIG. 10, where an emitter is a substantially flat emitter supported at a first end by two rods extending from a two-rod insulator assembly, and supported at a second end of the emitter by a compliant, single rod insulator assembly. The compliant, single rod insulator assembly of the second example X-ray emitter assembly includes a single rod directly coupled to the emitter. FIGS. 11-13 show detailed views of the compliant, single rod insulator assembly of the second example X-ray emitter assembly, including a first, a second, and a third example of the compliant, single rod insulator assembly. FIGS. 3-12 are shown approximately to scale, although other relative dimensions may be used.

Conventional X-ray imaging systems may use one of two types of emitters positioned in a focusing cup of a cathode of an X-ray tube to emit electrons and generate X-ray beams. An electric current is transmitted through the emitter and heats the emitter to emit electrons. A first type of emitter is a coiled tungsten filament. A second type of emitter is a flat emitter having a substantially planar surface. Rather than being formed of a coiled filament/wire, the flat emitter, also referred to as a ribbon emitter, is a substantially flat sheet of tungsten with a serpentine pattern cut through the flat sheet. The flat emitter may be more efficient than the coiled emitter because the flat surface of the emitter provides more focused emission of electrons and emits more electrons per surface area compared to the coiled filament. An ongoing goal of X-ray tube development is to design a more emissive emitter that provides a brighter electron source (e.g., more electrons per surface area).

In conventional X-ray tube designs, the emitter may be suspended and/or positioned on insulators in the cathode cup. Electric current may be provided to the emitter via a first source at a first end of the emitter. The current may travel along the serpentine pattern of the flat emitter to heat up emitter and cause electron emission. Heating the emitter also causes thermal expansion of the emitter. However, if the flat emitter is fixed in space, thermal expansion of the flat emitter may cause ligaments of the serpentine pattern of the emitter to touch and short out. Additionally, the G load in the radial direction caused by rotating of the X-ray tube may push on the emitter and causes the emitter to compress like a spring. Compression causes ligaments of the serpentine pattern to compress and touch, which short out the emitter.

Generating X-ray beams for imaging further includes rotating the X-ray tube around an imaging area for acquiring the projection data, for example, at different energy levels. Rotating the X-ray tube about a central axis imparts a centrifugal force on the X-ray tube, and therefore on the emitter. The centrifugal force may be, for example, 50 G or more. The centrifugal force is felt by the emitter and may cause the emitter to move and short out. For example, the emitter may move within the cathode cup and/or may deform in shape, which may cause coils of the coiled wire or sections of the serpentine pattern of the flat emitter to touch each other, and/or to touch the cathode cup, and short out. This is undesirable, as shorting may degrade the emitter and render the emitter, and therefore the X-ray tube, inoperable. Thus, it is desirable to prevent shorting of the emitter when high external force (e.g., centrifugal force due to rotation) is applied to the emitter.

A design for an emitter is thus desired that is resistant to shorts caused by thermal expansion, movement, and compression of the emitter. Described herein is a substantially flat emitter, comprising a first end of an emitter supported by two rods extending from a two-rod insulator assembly and a second end of the emitter supported by a compliant, single rod insulator assembly. The first end of the emitter is fixed in place (e.g., in a cathode cup) by the two-rod insulator assembly, and a position of the second end of the emitter may be axially and vertically adjustable via the compliant, single rod insulator. The two-rod insulator assembly provides an electrical current input and an electrical current output for the emitter in a coplanar, single insulator assembly. Coplanar positioning of the two rods as well as variable height positioning of the compliant, single rod insulator assembly enables a planar positioning of the emitter, which may remove deforming forces imposed in a vertical direction (e.g., perpendicular to a planar surface of the emitter) that are present in conventional emitter assemblies. The emitter may have a variety of configurations, including a single pass emitter or a dual pass emitter. Additionally, the compliant, single rod insulator assembly may have various configurations that enable movement and thermal expansion of the emitter. As described herein, "compliant" defines a flexible element, mechanism, or assembly that achieves force and motion transmission through elastic body deformation. In a first example, the compliant, single rod insulator comprises a substantially flat support plate comprising a socket, where the emitter is inserted into the socket and the substantially flat support plate is perpendicular to the emitter. A compliant section of the compliant, single rod insulator assembly may be at an emitter-support plate interface, and in other examples, the compliant region may be at a support plate-single rod interface. The emitter may move within the socket of the substantially flat support plate, and/or the substantially flat support plate may move within a socket of the single rod, which may result from thermal expansion of the emitter during heating and/or due to rotation of the X-ray tube in which the emitter is positioned.

In a further example, the compliant, single rod insulator assembly may comprise an expansion joint coupled to the emitter, and the expansion joint inserted into a socket of a single rod of the compliant, single rod insulator assembly. An additional example of the compliant, single rod insulator assembly includes a single rod directly coupled to the emitter and coupled to the single rod extending from the insulator via a pin joint. The emitter may move within the socket of the single rod, the expansion joint and the emitter may move with respect to the single rod, and/or the emitter may move with respect to the single rod via the pin joint, which may result from thermal expansion of the emitter during heating and/or due to rotation of the X-ray tube in which the emitter is positioned. Each embodiment of the emitter, the two-rod insulator assembly, and the compliant, single rod insulator assembly enables thermal expansion of the emitter and movement of the emitter in response to centrifugal forces and heating of the emitter in such a way that shorting of the emitter due to touching of the serpentine pattern ligaments to each other and/or to the cathode cup may be avoided.

Technical advantages of the herein disclosed system include a simple and compact emitter for generating X-ray beams that does not significantly increase a complexity, footprint, or weight of the X-ray emitter assembly while simultaneously increasing an efficiency of the emitter by reducing degradation of the emitter due to shorting and increasing a surface area for electron emission. Additionally, focusing accuracy of the electron beam may be increased using the X-ray emitter configuration described herein, compared to a conventional coiled filament, because the electrons are being projected from a planar surface of the substantially flat emitter.

Before further discussion of the substantially flat emitter with a fixed end and a compliant end, an example imaging system in which the emitter may be implemented is shown.

Turning now to FIG. 1, a block diagram is shown of an embodiment of an imaging system 100 configured both to acquire original image data and to process the image data for display and/or analysis in accordance with exemplary embodiments. It will be appreciated that various embodiments are applicable to numerous X-ray imaging systems implementing an X-ray tube, such as X-ray radiography (RAD) imaging systems, X-ray mammography imaging systems, fluoroscopic imaging systems, tomographic imaging systems, or CT imaging systems. The following discussion of the imaging system 100 is merely an example of one such implementation and is not intended to be limiting in terms of modality.

As shown in FIG. 1, imaging system 100 includes an X-ray tube 112 configured to project a beam of X-rays 114 through an object 116. The object 116 may include a human subject, pieces of baggage, or other objects desired to be scanned. The X-ray tube 112 may be conventional X-ray tubes producing X-rays 114 having a spectrum of energies that range, typically, from thirty (30) keV to two hundred (200) keV. The X-rays 114 pass through the object 116 and, after being attenuated, impinge upon a detector assembly 118. Each detector module in the detector assembly 118 produces an analog electrical signal that represents the intensity of an impinging X-ray beam, and hence the attenuated beam, as it passes through the object 116. In one embodiment, detector assembly 118 is a scintillator based detector assembly, however, it is also envisioned that direct-conversion type detectors (e.g., CdTe, CZT, Si detectors, etc.) may also be implemented.

A processor 120 receives the signals from the detector assembly 118 and generates an image corresponding to the object 116 being scanned. A computer 122 communicates with the processor 120 to enable an operator, using an operator console 124, to control the scanning parameters and to view the generated image. That is, the operator console 124 includes some form of operator interface, such as a keyboard, mouse, voice activated controller, or any other suitable input apparatus that allows an operator to control the imaging system 100 and view the reconstructed image or other data from the computer 122 on a display unit 126. Additionally, the operator console 124 allows an operator to store the generated image in a storage device 128 which may include hard drives, floppy discs, compact discs, etc. The operator may also use the operator console 124 to provide commands and instructions to the computer 122 for controlling a source controller 130 that provides power and timing signals to the X-ray tube 112.

FIG. 2 illustrates an exemplary CT system 200 configured for CT imaging. The CT system 200 may be an example of the imaging system 100 of FIG. 1. Particularly, the CT system 200 is configured to image a subject 212 (e.g., the object 116 of FIG. 1) such as a patient, an inanimate object, one or more manufactured parts, and/or foreign objects such as dental implants, stents, and/or contrast agents present within the body. In one embodiment, the CT system 200 includes a gantry 202, which in turn, may further include at least one X-ray tube 204 (e.g., the X-ray tube 112) configured to project a beam of X-ray radiation (e.g., the beam of X-rays 114) for use in imaging the subject 212 laying on a table 214. Specifically, the X-ray tube 204 is configured to project the X-ray radiation beams towards a detector array 208 (e.g., the detector assembly 118) positioned on the opposite side of the gantry 202. In certain embodiments, the X-ray tube 204 is configured to traverse different angular positions around the subject 212 for acquiring desired projection data. Accordingly, the gantry 202 and the components mounted thereon may be configured to rotate about a center of rotation 206 for acquiring the projection data, for example, at different energy levels. Alternatively, in embodiments where a projection angle relative to the subject 212 varies as a function of time, the mounted components may be configured to move along a general curve rather than along a segment of a circle.

Although FIG. 2 depicts a single X-ray tube 204, in certain embodiments, multiple X-ray tubes and detectors may be employed to project a plurality of X-ray radiation beams for acquiring projection data at different energy levels corresponding to the patient. In some embodiments, the X-ray tube 204 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray tubes and detectors are used to generate dual-energy projections, with one set at low-kVp and the other at high-kVp. It should thus be appreciated that the methods described herein may be implemented with single energy acquisition techniques as well as dual energy acquisition techniques.

In some CT imaging system configurations, an X-ray tube projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of a radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray tube and the detector array are rotated with a gantry within the imaging plane and around the object to be imaged such that an angle at which the radiation beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray tube and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as MLEM and orderedsubsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

FIG. 3 illustrates a cross-sectional schematic view of an X-ray tube 300 which may be included in the imaging system of FIGS. 1 and/or 2. For example, the X-ray tube 300 may be an exemplary embodiment of the X-ray tube 112 of FIG. 1 and/or the X-ray tube 204 of FIG. 2. The X-ray tube 300 comprises an anode 348, a cathode 352, and a cathode cup 362 of the cathode 352. An axis system 301 is provided in FIGS. 3-13 for reference. The z-axis may be a vertical axis (e.g., parallel to a gravitational axis), the y-axis may be a lateral axis (e.g., horizontal axis), and the x-axis may be a longitudinal axis, in one example. However, the axes may have other orientations, in other examples. As further described herein with respect to FIGS. 4-13, the X-ray tube 300 further comprises an emitter assembly positioned in the cathode cup 362, the emitter assembly comprising an emitter with a first end supported by two rods extending from a two-rod insulator assembly, and a second end of the emitter supported by a compliant, single rod insulator assembly. Before further discussion of the emitter assembly, an example X-ray tube in which the emitter assembly may be implemented is shown.

The X-ray tube 300 includes an anode assembly 342 and a cathode assembly 344 within a frame 346, which houses the anode 348 with a target 366, a bearing assembly 350, and a cathode 352. The frame 346 defines an area of relatively low pressure (e.g., a vacuum) compared to ambient, in which high voltages may be present. Further, the frame 346 may be positioned within a casing (not shown) filled with a cooling medium, such as oil, that may also provide high voltage insulation. While the anode 348 and the target 366 are described above as being a common component of the X-ray tube 300, the anode 348 and target 366 may be separate components in alternative X-ray tube embodiments.

In operation, an electron beam is produced by the cathode assembly 344. In particular, an emitter assembly of the cathode 352 receives one or more electrical signals via a series of electrical leads 356. The electrical signal(s) heat up an emitter of the emitter assembly, causing the emitter to emit electrons in an electron beam. The electron beam occupies a space 354 between the cathode 352 and the target 366 of the anode 348. The electrical signals may be timing/control signals that cause the cathode 352 to emit the electron beam at one or more energies and at one or more frequencies. The electrical signals may also at least partially control the potential between the cathode 352 and the anode 348. Cathode 352 includes a central insulating shell 358 from which a mask 360 extends. Mask 360 encloses electrical leads 356, which extend to the cathode cup 362 mounted at the end of mask 360. In some embodiments, cathode cup 362 serves as an electrostatic lens that focuses electrons emitted from an emitter within cathode cup 362 to form the electron beam.

X-rays 364 are produced when high-speed electrons of the electron beam are suddenly decelerated when directed from the cathode 352 to the target 366 formed on the anode 348 via a potential difference therebetween of, for example, sixty thousand (60,000) volts or more in the case of CT applications. The X-rays 364 are emitted through a radiation emission passage 368 formed in the frame 346 toward a detector array, such as the detector assembly 118 of FIG. 1 and/or the detector 208 of FIG. 2.

Anode assembly 342 includes a rotor 372 and a stator (not shown) located outside the X-ray tube 300 and surrounding the rotor 372 for causing rotation of the anode 348 during operation. The anode 348 is supported for rotation by a bearing assembly 350, which, when rotated, also causes the anode 348 to rotate about a centerline 370 thereof. As such, the centerline 370 defines a rotational axis of the anode 348 and the bearing assembly 350. As shown, the anode 348 has an annular shape, which contains a circular opening 374 in the center thereof for receiving the bearing assembly 350.

The anode 348 may be manufactured to include a number of metals or alloys, such as tungsten, molybdenum, copper, or any material that contributes to bremsstrahlung (e.g., deceleration radiation) when bombarded with electrons. The target 366 of the anode 348 may be selected to have a relatively high refractory value so as to withstand the heat generated by electrons impacting the anode 348. Further, the space between the cathode assembly 344 and the anode 348 is evacuated (e.g., as part of the vacuum of the X-ray tube 300) in order to minimize electron collisions with other atoms and to maximize an electric potential.

To avoid overheating of the anode 348 when bombarded by the electrons, the rotor 372 rotates the anode 348 at a high rate of speed (e.g., 90 to 250 Hz) about the centerline 370. In addition to the rotation of the anode 348 within the frame 346, in a CT application, the X-ray tube 300 as a whole is caused to rotate about an object, such as the object 116 of the imaging system 100 in FIG. 1, at rates of typically 1 Hz or faster. For example, as described with respect to FIG. 2, the gantry 202 and elements thereof (e.g., including the X-ray tube 204) may be configured to rotate about the center of rotation 206.

Different embodiments of the bearing assembly 350 can be formed, such as with a number of suitable ball bearings, but in the illustrated exemplary embodiment comprises a liquid metal hydrodynamic bearing having adequate load-bearing capability and acceptable acoustic noise levels for operation within the imaging system 100 of FIG. 1.

In general, the bearing assembly 350 includes a stationary component, such as a center shaft 376, and a rotating portion, such as a sleeve 378 to which the anode 348 is attached. While the center shaft 376 is described with respect to FIG. 3 as the stationary component of the bearing assembly 350 and the sleeve 378 is described as the rotating component of the bearing assembly 350, embodiments of the present disclosure are also applicable to embodiments wherein the center shaft 376 is a rotary shaft and the sleeve 378 is a stationary component. In such a configuration, the anode 348 would rotate as the center shaft 376 rotates.

The center shaft 376 may optionally include a coolant flow path 380 though which a coolant (not shown), such as oil, may flow to cool the bearing assembly 350. As such, the coolant enables heat generated from the anode 348 of the X-ray tube 300 to be extracted therefrom and transferred external from the X-ray tube 300. In straddle mounted X-ray tube configurations, the coolant flow path 380 extends along a longitudinal length of the X-ray tube 300, e.g., along the centerline 370. In alternative embodiments, the coolant flow path 380 may extend through a portion of the X-ray tube 300, such as in configurations where the X-ray tube 300 is cantilevered when placed in an imaging system.

Figure 4:
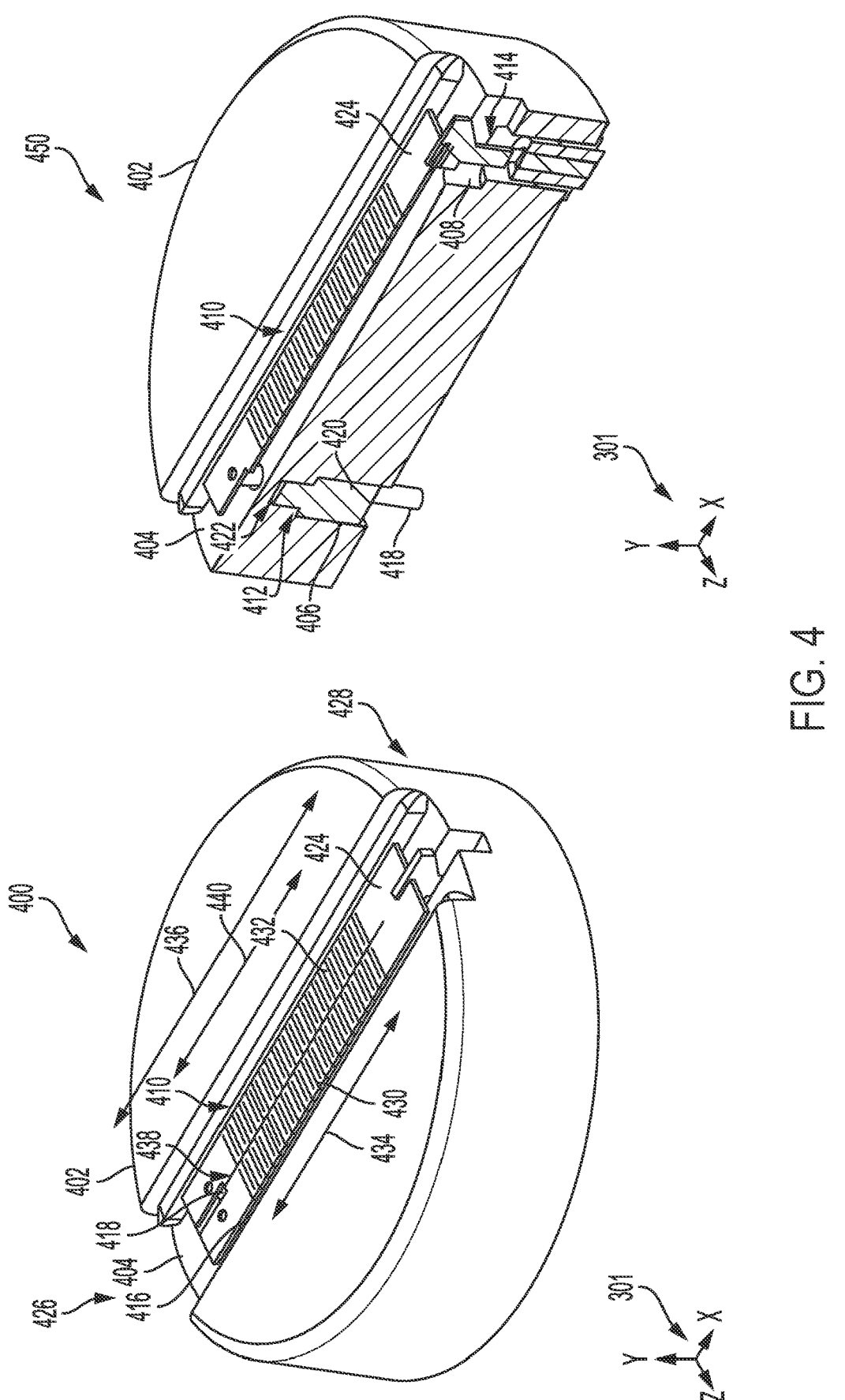
FIG. 4 shows perspective views of a cathode of an X-ray tube, such as the X-ray tube of FIG. 3.

As described briefly with respect to FIG. 3, the cathode cup 362 may serve as an electrostatic lens that focuses electrons emitted from an emitter within cathode cup 362 to form the electron beam. FIG. 4 shows a perspective view 400 and a cross-sectional perspective view 450 of a cathode cup 402 with an X-ray emitter assembly 410 positioned therein. The cathode cup 362 may be an example of the cathode cup 362 of FIG. 3. The X-ray emitter assembly 410 may have various configurations comprising a first end of a substantially flat emitter supported by two rods extending from a two-rod insulator assembly, a second end of the substantially flat emitter supported by a compliant, single rod insulator assembly. FIG. 4 shows a first example emitter assembly, as is further described with respect to FIGS. 5-9. A second example X-ray emitter assembly may alternatively be positioned in the cathode cup 362 without departing from the scope of the present disclosure, as described with respect to FIGS. 10-13.

The cathode cup 362 of FIG. 4 has a cylindrical shape with a central cutout 404 for positioning the X-ray emitter assembly 410 therein. As shown in the cross-sectional perspective view 450, the central cutout 404 comprises a partial channel 406 in which a two-rod insulator assembly 412 of the X-ray emitter assembly 410 is positioned, and a through channel 408 in which a compliant, single rod insulator assembly 414 of the X-ray emitter assembly 410 is positioned. The two-rod insulator assembly 412 comprises a first rod 416 and a second rod 418 extending from a two-rod insulator 420. The two-rod insulator assembly 412 may be brazed into the cathode cup 362 at the partial channel 406. In other examples, the two-rod insulator assembly 412 may be welded into the cathode cup 362 at the partial channel 406. The two-rod insulator 420 may be vertically spaced apart from the cathode cup 362, such that there may be a space 422 therebetween. The first rod 416 and the second rod 418 extend from the two-rod insulator 420, through the space 422, and to an emitter 424 of the X-ray emitter assembly 410. The two-rod insulator assembly 412 positions the X-ray emitter assembly 410 in the cathode cup 362 in such a way that the emitter 424 is rigidly supported at a first end 426 of the emitter 424. The compliant, single rod insulator assembly 414 may have various configurations, as further described herein. Generally, the compliant, single rod insulator assembly 414 positions the emitter 424 in the cathode cup 362 in such a way that the emitter 424 is compliantly supported at a second end 428 of the emitter 424. Compliant support of the emitter 424 by the compliant, single rod insulator assembly 414 applies rigid radial support (e.g., along the z-axis and the y-axis) to the emitter 424 and enables axial movement (e.g., along the x-axis) the emitter 424. Radial and axial directions are described herein with respect to the cathode cup 362. Further detail regarding each of the two-rod insulator assembly 412 and the compliant, single rod insulator assembly 414 are described with respect to FIGS. 5-13. The cathode cup 362 may be formed at least in part by molybdenum.

The emitter 424 is a substantially flat emitter having a planar emission surface. As shown in FIG. 4, the emitter 424 is a two-pass ribbon emitter with the planar emission surface comprising a first pass 430 and a second pass 432 each having a serpentine pattern along a first portion 434 of a length 436 of the emitter 424. The first pass 430 and the second pass 432 may be spaced apart from each other by a gap 438 for a second portion 440 of the length 436 of the emitter 424, the second portion 440 including the first portion 434. The serpentine pattern comprises a series of ligaments that are connected and have gaps between each curve of the serpentine pattern. Between the first pass 430 and the second pass 432 at the first end 426, the gap 438 may have a greater width (e.g., along the x-axis) than that of the gap 438 between the first pass 430 and the second pass 432 along the second portion 440 of the length 436. At the first end 426, the emitter may comprise a first through hole 448 and a second through hole 452 that are radially aligned and may provide ventilation for rods of the two-rod insulator assembly 412, as further described herein. The first pass 430 and the second pass 432 are connected at the second end 428 by a planar portion of the emitter 424 that does not include a serpentine pattern or through hole(s).

In other examples, the substantially flat emitter (e.g., the emitter 424) comprises a first end (e.g., the first end 426) supported by at least one rod (e.g., the first rod 416 and/or the second rod 418) extending from an insulator assembly (e.g., the insulator assembly 412), and a second end (e.g., the second end 428) supported by a substantially flat support plate comprising a socket, where the second end is inserted into the socket and the substantially flat support plate is perpendicular to a planar emission surface. This configuration is a variation of the configuration shown in FIG. 4, and may be used when the emitter 424 is configured as a single pass emitter. In some examples, the emitter 424 may be a single pass emitter with a serpentine pattern. For example, the first pass 430 and the second pass 432 of the two-pass ribbon emitter may be formed as a single pass, with no gap 438 therebetween. The serpentine pattern may extend a width of the emitter 424 in the single pass emitter, rather than a first serpentine path of the first pass 430 extending half of the width (e.g., along the x-axis) of the emitter 424 (e.g., a width of the first pass 430) and a second serpentine path of the second pass 432 extending half of the width of the emitter 424 (e.g., a width of the second pass 432). The single pass emitter is supported on a first side (e.g., at the first end 426, with respect to the emitter 424) by a variation of the two-rod insulator assembly 412. The variation of the two-rod insulator assembly 412 configured for the single pass emitter comprises a single rod (e.g., the first rod 416) that extends through an insulator configured with a single filament feedthrough channel. The insulator may be formed of ceramic and/or of another material or combination of materials that sufficiently insulates the cathode cup 362 from the single rod. The single rod may be welded or brazed in the insulator, in some embodiments. In other examples, the single rod may not be fixedly coupled to the insulator. The single rod may be formed of niobium, or other conductive material. The single pass emitter is supported on a second side, opposite the first side (e.g., at the second end 428, with respect to the emitter 424) by the compliant, single rod insulator assembly 414.

Figure 5:
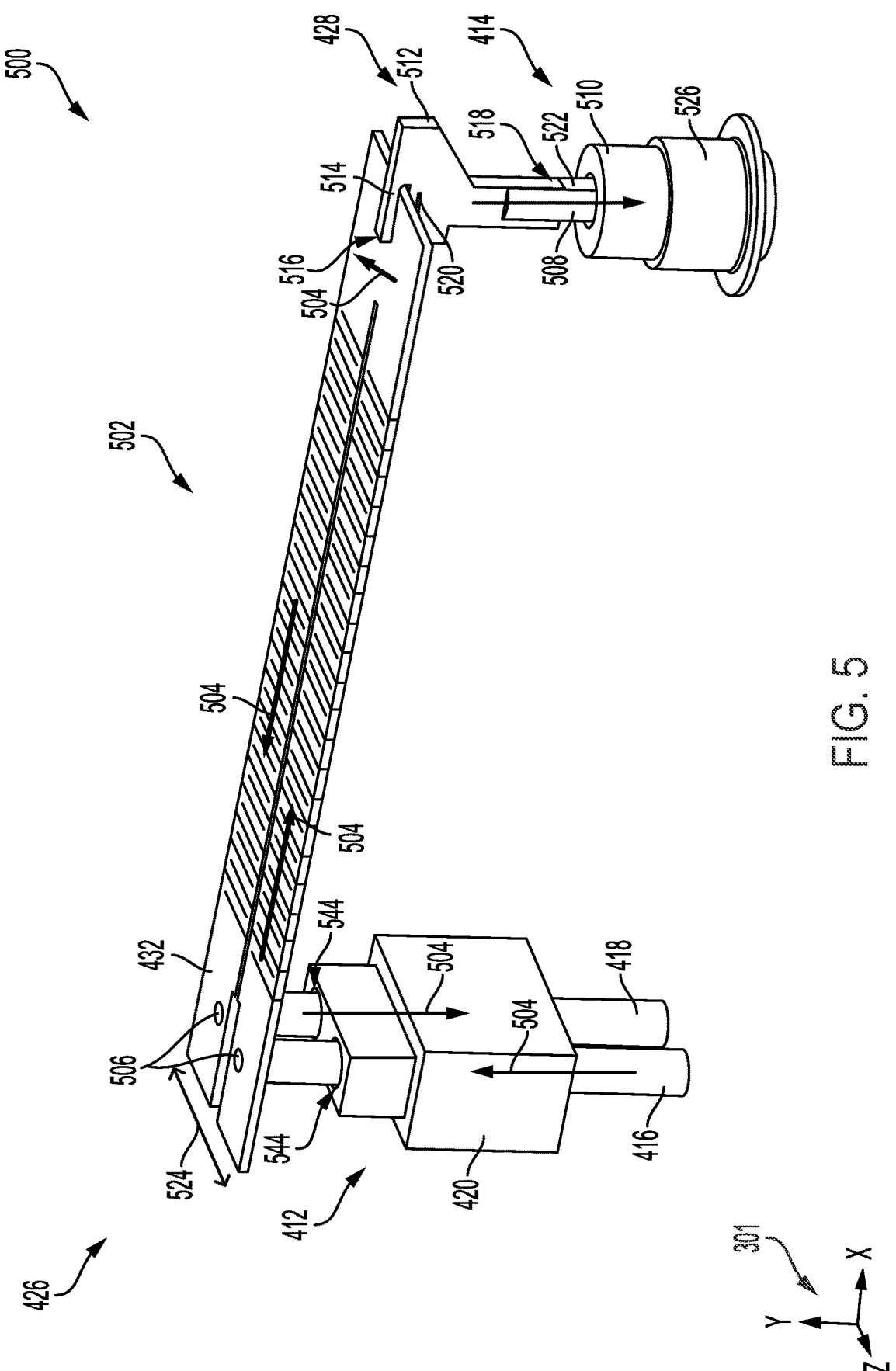
FIG. 5 shows a perspective view of a first example X-ray emitter assembly of the cathode of FIG. 4.

FIG. 5 shows a perspective view 500 of a first example emitter assembly 502, which may be implemented as the X-ray emitter assembly 410 of FIG. 4. Elements of the first example emitter assembly 502 described with respect to FIG. 4 are equivalently numbered. As described with respect to FIG. 4, the first end 426 of the emitter 424 is rigidly supported by the two-rod insulator assembly 412, and the second end 428 of the emitter 424 is compliantly supported by the compliant, single rod insulator assembly 414. Rigid support of the emitter 424 by the two-rod insulator assembly 412 may prevent movement (e.g., radial and axial movement) of the first end 426 of the emitter 424 within the cathode cup 362. Compliant support of the emitter 424 by the compliant, single rod insulator assembly 414 may prevent radial movement of the emitter 424 and enable axial movement of the emitter 424. The rigid and compliant supports of the emitter 424 enable partial movement of the emitter 424, such as thermal expansion in the axial direction (e.g., along the x-axis), which may prevent compression of the serpentine pattern of the emitter 424 and prevent shorting of the emitter 424 due to touching of the ligaments.

Electric current may be provided to the emitter 424 by one or more of the first rod 416 and the second rod 418 of the two-rod insulator assembly 412 to heat the emitter 424 and produce electrons therefrom, which may be used to generate X-ray beams as described with respect to FIG. 3. The electric current is an example of a heating current that heats the emitter 424. As shown by a series of arrows 504, an electric current may travel up the first rod 416, along the length 436 of the emitter 424 in the serpentine pattern from the first end 426 to the second end 428, along the length 436 of the emitter 424 in the serpentine pattern from the second end 428 to the first end 426, and out of the emitter 424 via the second rod 418. In another example, electric current may travel from both of the first rod 416 and the second rod 418 to a support plate 512, such that electric current travels from the first end 426 to the second end 428 and exits the emitter 424 via a single rod 508 of the compliant, single rod insulator assembly 414. Current feedthroughs at the first end 426 and the second end 428 are thus coplanar. The single rod 508 may not be electrically conductive and may act to compliantly support the emitter 424. In some embodiments where the emitter 424 is configured as a single pass emitter, the compliant, single rod insulator assembly 414 may be electrically insulated and configured to act as a compliant electric connection, as well as a compliant support.

The first end 426 of the emitter 424 is spot welded to each of the first rod 416 and the second rod 418 to secure the emitter 424 in space at the first end 426. If the emitter 424 were fixed in space at the second end 428 as well as at the first end 426, the emitter 424 may experience G forces from centrifugal forces enacted on the emitter 424 during rotation of the X-ray tube without having an outlet or space for the emitter 424 to move/deform, other than compression of the ligaments of the serpentine pattern. Compression of the ligaments of the serpentine pattern may lead to two or more of the ligaments being in contact, which may result in the emitter 424 shorting out and no longer functioning to emit electrons. The compliant, single rod insulator assembly 414 at the second end 428 of the emitter 424 further provides a current return path for electric current flowing through the emitter 424 to return to an electric current generator of the X-ray tube. The first example emitter assembly 502 described herein thus simultaneously solves for thermal expansion of, and G force applied to, the emitter 424 of the X-ray tube.

The two-rod insulator assembly 412 comprises the first rod 416 and the second rod 418 extending from the two-rod insulator 420. The two-rod insulator 420 is a ceramic insulator (e.g., formed of ceramic). In other embodiments, the two-rod insulator 420 may be formed of another material or combination of materials that sufficiently insulates the cathode cup 362 from the first rod and the second rod 418. The first rod 416 and the second rod 418 may be welded or brazed in the two-rod insulator 420, in some embodiments. In other examples, the first rod 416 and the second rod 418 may not be fixedly coupled to the two-rod insulator 420. The two-rod insulator 420 comprises two filament feedthrough channels 544 in which the first rod 416 and the second rod 418 are positioned. The first rod 416 and the second rod 418 are brazed to the two-rod insulator 420. The first rod 416 and the second rod 418 may be formed of niobium, or other conductive material.

The first rod 416 and the second rod 418 may provide electrical current to the emitter 424, and may be examples of the electrical leads 356 of the X-ray tube 300. The first rod 416 and the second rod 418 are fixedly coupled to the emitter 424 at a top surface 506 of each of the first rod 416 and the second rod 418. For example, each of the first rod 416 and the second rod 418 may be coupled to the emitter 424 via a Tungsten-Niobium weld. As described with respect to FIG. 4, the emitter 424 may comprise through holes 448, 452 that are vertically aligned with each of the first rod 416 and the second rod 418. The through holes 448, 452 may have a smaller diameter than a diameter of the first rod 416 and the second rod 418, and may provide ventilation for each of the first rod 416 and the second rod 418. The first rod 416 and the second rod 418 are machined, for example, via EDM, such that top surfaces of first rod and the second rod 418 are coplanar. EDM of the first rod 416 and the second rod 418 at an interface with the emitter 424 may remove distorting forces on the emitter that may be present when the first rod 416 and the second rod are at different heights. This enables the emitter to be positioned planar on top of the first rod 416 and the second rod 418, where there is no height difference between the first pass 430 and the second pass 432 of the emitter 424 (e.g., the first pass 430 and the second pass 432 are coplanar, there is no vertical deformation along the y-axis between the first pass 430 and the second pass 432). The design further provides compliance support of the emitter 424 while not significantly increasing a footprint of the X-ray emitter assembly 410. This enables potential inclusion of one or more additional emitters, which may be stacked in the cathode cup 362. For example, a second emitter may be positioned in the cathode cup 362, parallel to the emitter 424.

The compliant, single rod insulator assembly 414 at the second end 428 of the emitter 424 comprises a single rod 508 extending from an insulator 510, and the support plate 512 coupled to the single rod 508 and to the emitter 424. The single rod 508 is configured to apply rigid radial support (e.g., along the z-axis) to the emitter 424, and enable axial movement (e.g., along the x-axis) of the emitter 424. The support plate 512 may be formed of niobium, for example, and may be gold electroplated to provide electrical conductivity to the emitter 424 and the single rod 508. The single rod 508 may be formed of copper or another conductive material.

The support plate 512 may be a substantially flat support plate with at least a first socket 514. The first socket 514 is configured to have the emitter 424 positioned therein and hold the emitter 424 in space while providing expansion space for the emitter 424 to thermally expand without compression of the emitter 424 and without resulting in a compressive force on ligaments of the emitter 424. The support plate 512 is positioned perpendicular to the emitter 424, such that the first socket 514 is parallel to the length 436 of the emitter 424. The second end 428 of the emitter 424 may be inserted into the first socket 514 of the substantially flat support plate 512. As further described with respect to FIGS. 7-9, a compliant region of the compliant, single rod insulator assembly 414 may be at an emitter-support plate interface 516, and in other examples, the compliant region may be at a support plate-single rod interface 518. In some examples, the substantially flat support plate 512 further comprises a second socket 520, which may be parallel to and the same or a different length as the first socket 514.

The single rod 508 comprises a third socket 522 into which the support plate 512 is positioned. The compliant, single rod insulator assembly 414 may be positioned with respect to the emitter 424 such that the single rod 508 and the support plate 512 are positioned at an approximate center of a width 524 of the emitter 424. The single rod 508 may be aligned with the gap 438 between the first pass 430 and the second pass 432 of the emitter, as described with respect to FIG. 4. The support plate 512 may have friction interference with the single rod 508, such that the support plate 512 snaps and/or clips into the third socket 522 of the single rod 508. An interface of the support plate 512 and the third socket 522 may prevent vertical movement of the emitter 424 (e.g., along the y-axis). This enables the emitter 424 to expand radially to relieve stress from thermal expansion, due to heating of the emitter, and G force compression of the emitter due to rotation/spinning of the X-ray tube of the emitter, thus preventing shorting of the emitter 424. The insulator 510 of the compliant, single rod insulator assembly 414 may have a cylindrical shape, and the single rod 508 may pass through a center of the insulator 510. A support ring 526 may circumferentially surround at least a portion of the insulator 510 and be positioned between the insulator 510 and the cathode cup 362 to position the insulator 510 therein. Further detail of the compliant, single rod insulator assembly 414 is described with respect to FIGS. 7-9.

As described above, the planar emission surface of the emitter 424 is positioned using the coplanar top surfaces of the first rod 416 and the second rod 418. With the compliant support on the second end 428 of the emitter 424, a vertical position of the emitter 424 at the second end 428 may be adjusted such that the planar emission surface is coplanar (e.g., in the z-x plane) along the length of the emitter 424. For example, the second end 428 of the emitter 424 may be positioned in the first socket 514 or the second socket 520 of the support plate 512. A vertical position of the emitter 424 may be additionally or alternatively adjusted by adjusting a position of the support plate 512 in the single rod 508, and/or adjusting a position of the single rod 508 in the insulator 510. The configuration of the compliant, single rod insulator 510 thus provides multiple points at which the vertical position of the emitter 424 may be adjusted to provide the emitter 424 with a planar configuration that extends from the first end 426 to the second end 428. Positioning the emitter 424 to be planar in the cathode cup 362 may assist in reducing distorting forces applied to the emitter 424 during heating of the emitter 424 (e.g., during thermal expansion of the emitter 424) and distorting forces from G force from rotation of the X-ray beam.

FIG. 6 shows a perspective view 600 of the two-rod insulator assembly 412 coupled to the emitter 424. The two-rod insulator assembly 412 is configured to provide rigid support to the emitter 424 and position the emitter 424 in the cathode cup 362, described with respect to FIGS. 4-5. As described above, electric current may be provided to the emitter 424 via one or more of the first rod 416 and the second rod 418. The first rod 416 and the second rod 418 are insulated from the cathode cup 362, shown in FIG. 4, by the two-rod insulator 420, such that electric current is not transferred from the first rod 416 and/or the second rod 418 to the cathode cup 362. The two-rod insulator 420 may further insulate the first rod 416 and the second rod 418 from each other.

The two-rod insulator 420 described herein has a stepwise form that enables the two-rod insulator to be positioned in and brazed to the partial channel 406 of the cathode cup 362. In other examples, the two-rod insulator 420 may have a different configuration that sufficiently insulates the first rod 416 and the second rod 418 from the cathode cup 362, while also positioning the X-ray emitter assembly 410 in the cathode cup 362 and providing rigid support at the first end 426 of the emitter 424.

The first rod 416 and the second rod 418 are arranged such that a top surface 506 of each of the first rod 416 and the second rod 418 are coplanar. Each of the first rod 416 and the second rod 418 are coupled to the emitter 424 at a respective top surface 506. For example, the top surface 506 of the first rod 416 is coupled to the first pass 430 of the emitter 424, and the top surface 506 of the second rod 418 is coupled to the second pass 432 of the emitter 424. As the top surface 506 of each of the first rod 416 and the second rod 418 are coplanar, the first pass 430 and the second pass 432 of the emitter 424 are coplanar. Described another way, there may be no height difference (e.g., along the y-axis) between the first pass 430 and the second pass 432. Coplanar positioning of the first pass 430 and the second pass 432 of the emitter 424 may reduce deformation of the emitter 424 during thermal heating of the emitter 424 and/or due to centrifugal forces applied to the emitter 424 via rotation of the X-ray tube in which the emitter 424 is positioned.

FIG. 7 shows a side view 700 of a first example compliant, single rod insulator assembly 702, which is an example of the compliant, single rod insulator assembly 414 coupled to the emitter 424 of the first example emitter assembly 502. The first example compliant, single rod insulator assembly 702 is configured to provide compliant support to the emitter 424, applying rigid radial support and enabling axial movement (e.g., along the x-axis) of the emitter 424. The compliant support may enable movement of the emitter 424, which may result from thermal expansion of the emitter 424 during heating, and/or due to rotation of the X-ray tube in which the emitter 424 is positioned.

As briefly described above, the compliant, single rod insulator assembly 414 may have various configurations with different positioning of a compliant region. The compliant region may be at an emitter-support plate interface 516, and in other examples, the compliant region may be at a support plate-single rod interface 710. In a first example, the single rod 508 is welded to the support plate 512 at the support plate-single rod interface 710, and the compliant region is at the emitter-support plate interface 712. The single rod 508 may be welded to the support plate 512. For example, the single rod 508 may be welded to the support plate 512 via a Niobium-Niobium weld and/or another weld material. The emitter 424 is removably coupled to the support plate 512. For example, the emitter 424 may be positioned in the first socket 514 and may not be welded to the substantially flat support plate 512. A length 436 of the first socket 514, and a position of the substantially flat support plate 512 is designed such that the emitter 424 is not in face-sharing contact with an end of the first socket 514. The length of the first socket 514 may be configured such that the emitter 424 does not fully extend into the length of the first socket 514, thus providing space for thermal expansion of the emitter 424. The first socket 514 may provide friction interference between the support plate 512 and the emitter 424, which holds the second end 428 of the emitter 424 in place in the support plate 512 and secures the emitter 424 in a compliant fashion such that the emitter 424 may move in plane without distorting. In this way, the compliant, single rod insulator assembly 414 may be compliant to movement of the emitter 424 at the emitter-support plate interface 516, as the emitter 424 may move along a first axial direction, indicated by a first arrow 720.

In a second example, the emitter 424 is welded to the support plate 512 at the emitter-support plate interface 712 (e.g., within the first socket 514), and the compliant region is at the support plate-single rod interface 710. The emitter 424 may be positioned in the first socket 514 of the support plate 512 as described above, and be welded to the support plate 512. For example, the emitter 424 may be welded to the support plate 512 via a Tungsten-Niobium weld and/or another weld material. The support plate 512 may be positioned in, but may not be welded or otherwise fixedly coupled, to the single rod 508 at the third socket 522. The third socket 522 may be configured to provide friction interference between the support plate 512 and the single rod 508. Thermal expansion of the emitter 424 may be transferred to the support plate 512 via the Tungsten-Niobium weld at the emitter-support plate interface 712, such that the support plate 512 may thermally expand in a vertical direction (e.g., along the y-axis). Described another way, the support plate 512 may expand in a direction indicated by a second arrow 724, which may prevent the emitter 424 from vertically moving or distorting (e.g., out of the x-z plane).

Turning to FIG. 8, a perspective view 800 of the first example compliant, single rod insulator assembly 702 of FIG. 7 is shown. The perspective view 800 shows the support plate 512 positioned in the third socket 522 of the single rod 508. As described with respect to FIG. 7, in some examples of the compliant, single rod insulator assembly 414, the compliant region may be at an emitter-support plate interface 712, and in other examples, the compliant region may be at the support plate-single rod interface 710. The compliant region at the support plate-single rod interface 710 comprises an expansion space 806 into which the support plate 512 may expand in response to thermal expansion of the emitter 424.

Turning to FIG. 9, a cross section view 900 is shown of the first example compliant, single rod insulator assembly 702 described with respect to FIGS. 7-8 positioned in the cathode cup 362 of FIG. 4. As described with respect to FIGS. 4-5, the insulator 510, the single rod 508, and the support ring 526 of the compliant, single rod insulator assembly 414 may be positioned in the cathode cup 362 to provide rigid radial support and enable axial movement of the emitter 424. The support ring 526 may interface with a bottom surface 904 of the cathode cup 362, and the insulator 510 may be coupled to the support ring 526, such that the insulator 510 and the support ring 526 have fixed positions with respect to the cathode cup 362. Further, the single rod 508 may have a fixed position in the insulator 510. As described with respect to FIGS. 7-8, the compliant region of the first example compliant, single rod insulator assembly 702 may be at the emitter-support plate interface 712 or at the support plate-single rod interface 710. When the compliant region is at the emitter-support plate interface 712, the first socket 514 of the support plate 512 enables constrained longitudinal motion (e.g., along the x-axis) of the emitter 424 (e.g., in a direction indicated by a double-sided arrow 910). In this example, the support plate 512 is fixedly coupled to the single rod 508 (e.g., at the support plate-single rod interface 710). In examples where the compliant region is at the support plate-single rod interface 710, the emitter 424 is fixedly coupled to the support plate 512 at the first socket 514 (e.g., at the emitter-support plate interface 712), and the support plate 512 may move (e.g., thermally expand) within the third socket 522 of the single rod 508. For example, thermal expansion of the emitter 424 may be transmitted to and cause thermal expansion of the support plate 512. As shown in FIG. 8, an expansion space 806 in the third socket 522 between the single rod 508 and the support plate 512 may provide space for the support plate 512 to thermally expand and prevent compression of the emitter 424, where compression of the emitter 424 may lead to shorting out of the emitter 424. Relative motion of the X-ray emitter assembly 410 is directed away from the emitter 424 and to the support plate-single rod interface 710. In this example, the single rod 508 may be fixedly positioned in the insulator 510, and the insulator 510 may be fixedly positioned in the cathode cup 362 via the support ring 526. Both examples of positioning of the compliant region in the first example compliant, single rod insulator assembly thus provide rigid radial support and compliant axial support of the emitter 424.

Figure 10:
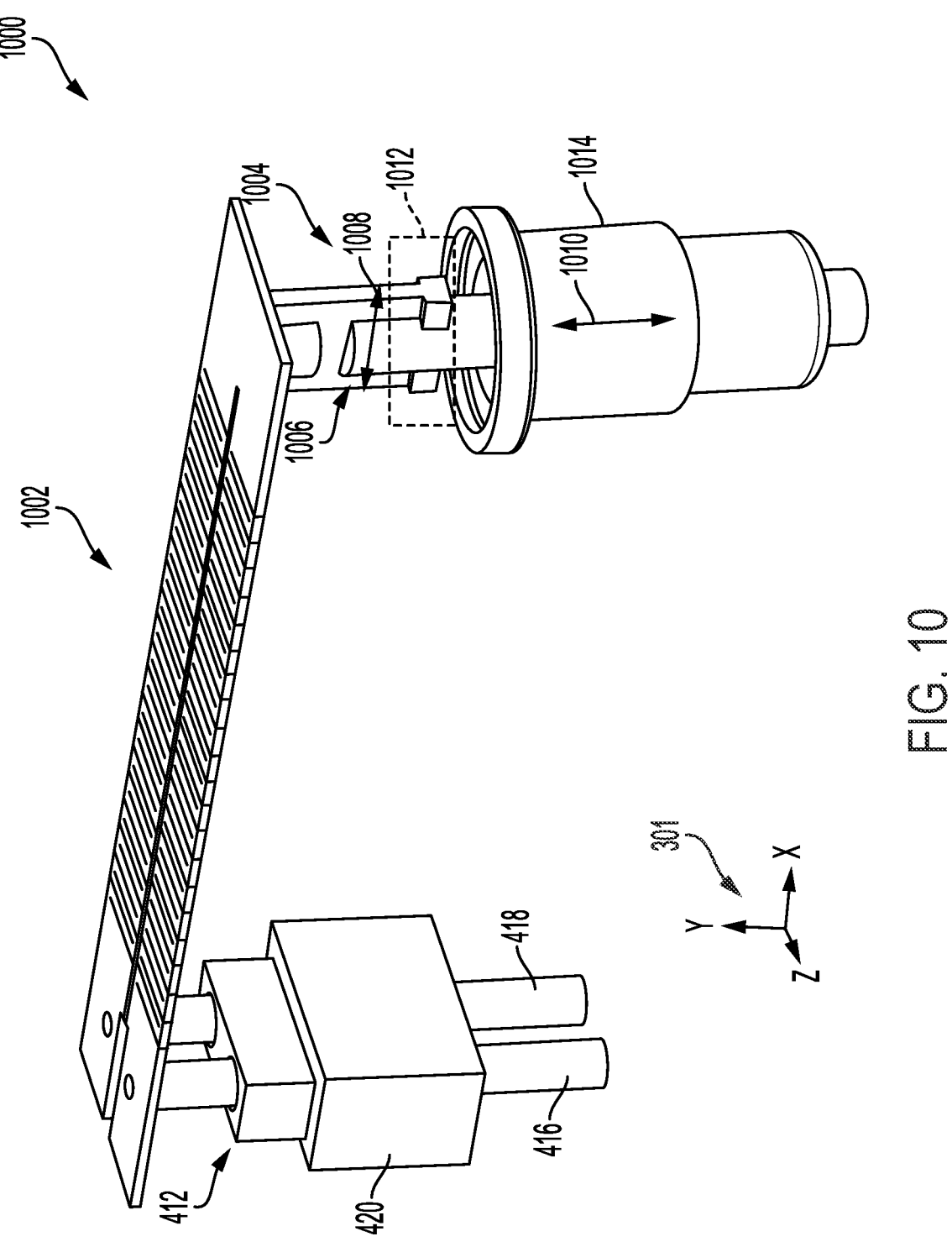
FIG. 10 shows a perspective view of a second example X-ray emitter assembly of the cathode of FIG. 4.
Figure 11:
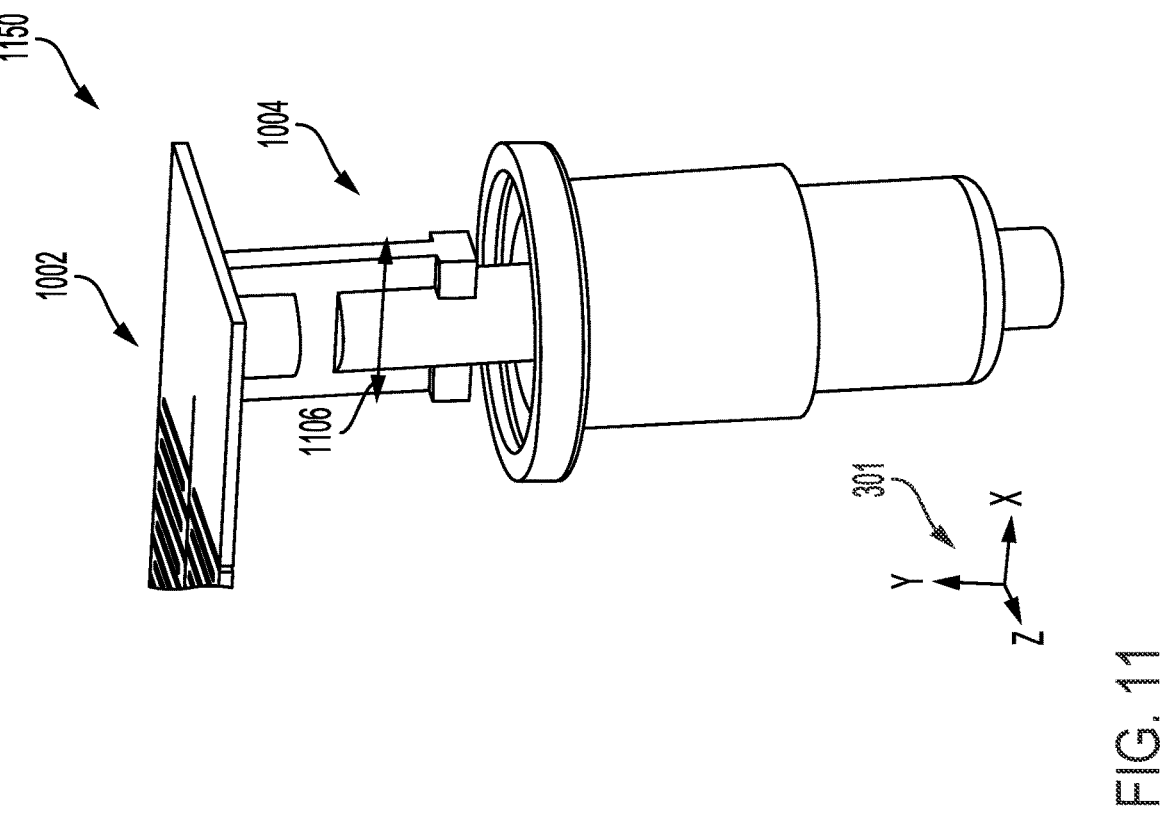
FIG. 11 shows perspective views of a second example of the compliant, single rod insulator assembly of the second example X-ray emitter assembly of FIG. 10.
Figure 11:
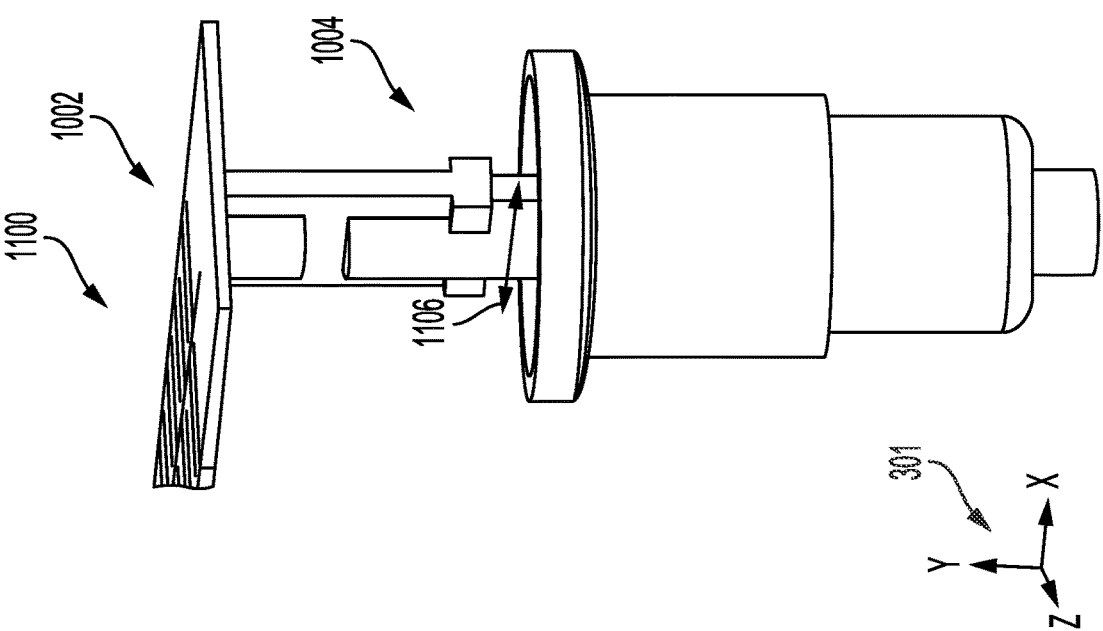
Figure 12:
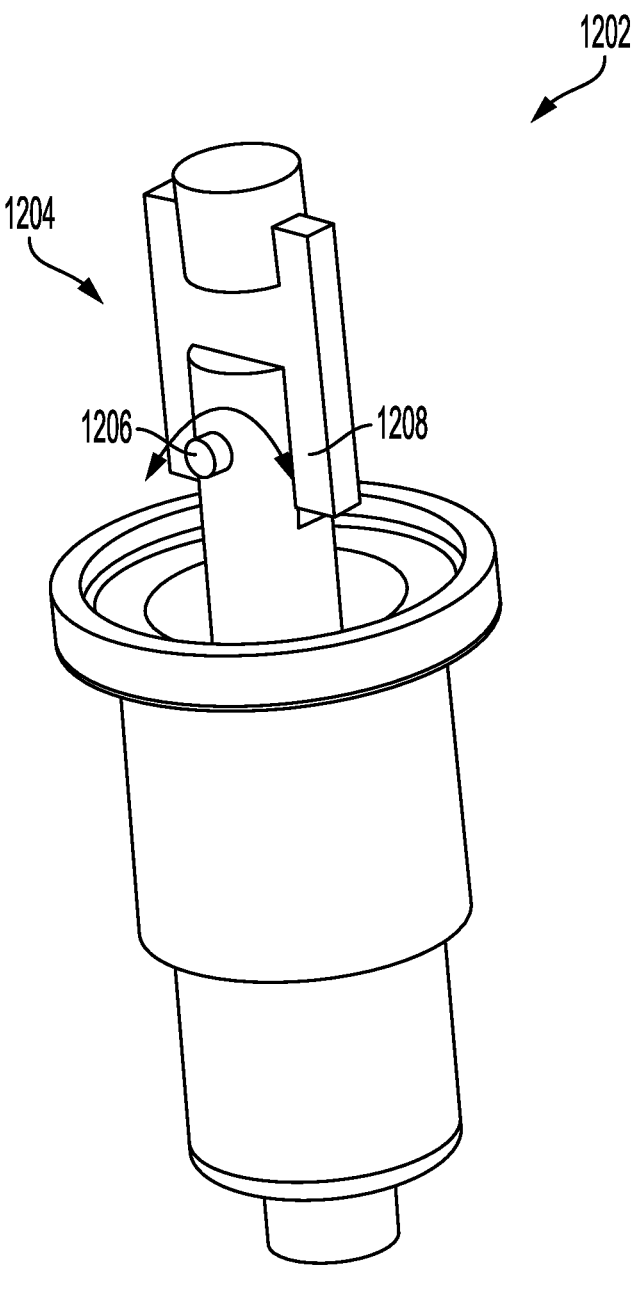
FIG. 12 shows a perspective view of a third example of the compliant, single rod insulator assembly of the second example X-ray emitter assembly of FIG. 10.
Figure 12:
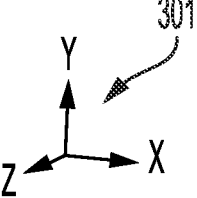
Figure 13:
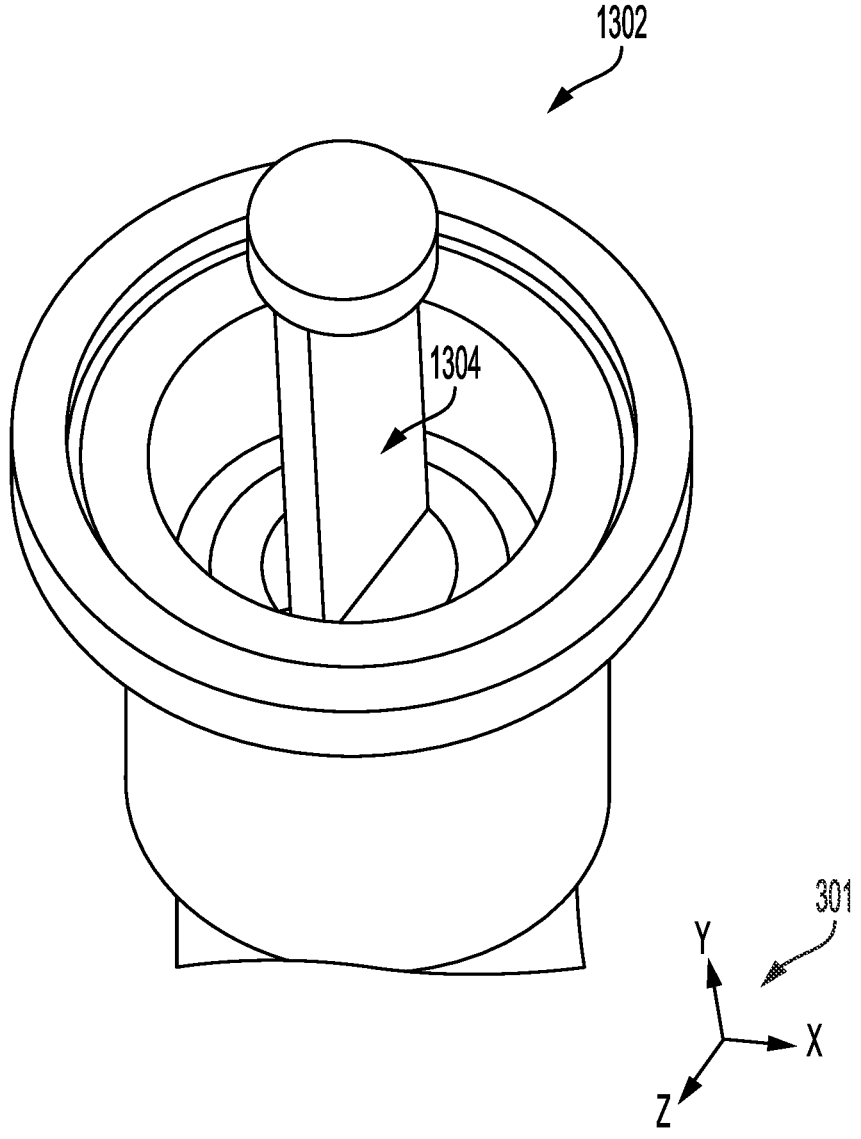
FIG. 13 shows a perspective view of a fourth example of the compliant, single rod insulator assembly of the second X-ray example emitter assembly of FIG. 10.

In some examples, as further described with respect to FIGS. 10-13, the compliant, single rod insulator assembly includes a single rod extending from an insulator, where the single rod is directly coupled to the emitter without a support plate therebetween. FIG. 10 shows a perspective view 1000 of a second example emitter assembly 1002. The second example emitter assembly 1002 is a variation of the first example emitter assembly 502 of FIGS. 4-9, and may include at least some of the same elements, which are equivalently numbered in FIGS. 10-13. The two-rod insulator assembly 412 of the second example emitter assembly 1002 has the same configuration as the two-rod insulator assembly 412 of the first example emitter assembly 502, and is configured to rigidly position the first end 426 of the emitter 424 in the cathode cup 362, preventing radial movement of the emitter 424 at the first end 426. The second example emitter assembly 1002 may be positioned in a cathode cup of an X-ray tube, such as the cathode cup 362 of FIG. 4, as described with respect to the first example emitter assembly 502 of FIGS. 4-9.

The second example emitter assembly 1002 comprises a second example compliant, single rod insulator assembly 1004, where a compliant region comprises an expansion joint 1006. As described with respect to FIGS. 7-9, the single rod 508 includes the third socket 522. In the second example compliant, single rod insulator assembly 1004, the expansion joint 1006 may be inserted into the third socket 522 of the single rod 508. The third socket 522 in the example of FIG. 10 is shaped to interlock with the expansion joint 1006, enabling lateral movement of the expansion joint 1006, indicated by a first double sided arrow 1008, and preventing vertical movement of the expansion joint 1006, indicated by a second double sided arrow 1010. The expansion joint 1006 is inserted into the third socket 522 of the single rod 508 at a first end 426 of the expansion joint 1006, and the expansion joint 1006 is coupled to the emitter 424 at a second end 428 of the expansion joint 1006, the second end 428 opposite the first end 426. The expansion joint 1006 may be welded or otherwise fixedly coupled to the emitter 424 at a top surface 506 of the expansion joint 1006, opposite an expansion joint-single rod interface 1012. The second example compliant, single rod insulator assembly 1004 further includes an insulator 510, which may be equivalent to the insulator 510, and a ring support 1014 that circumferentially surrounds at least a portion of the insulator 510 and may be used to fixedly position the insulator 510 and the single rod 508 in the cathode cup 362.

Turning to FIG. 11, a first perspective view 1100 and a second perspective view 1150 of the second example emitter assembly 1002 are shown. As described with respect to FIGS. 5-10, the single rod 508 comprises the third socket 522 configured to receive the expansion joint 1006. The expansion joint 1006 has a T-shape that, when inserted into the third socket 522 configured with a reciprocal T-shape, may be prevented from vertical movement (e.g., along the y-axis) and radial movement (e.g., along the z-axis). The expansion joint 1006 may not be welded or otherwise fixedly coupled to the third socket 522. Positioning of the expansion joint 1006 in the third socket 522 enables linear movement (e.g., along the x-axis) of the expansion joint 1006, and the emitter 424 coupled thereto at the top surface 506. For example, when the X-ray tube in which the emitter assembly is positioned (e.g., the X-ray tube 300 of FIG. 3) is rotated during an imaging operation, the emitter 424 may experience centrifugal forces. The two-rod insulator assembly 412, described with respect to FIGS. 4-10, fixedly/rigidly positions the emitter 424 in the cathode cup 362 at the first end 426 of the emitter 424. The second example emitter assembly 1002 transmits centrifugal forces on the emitter 424 into axial movement of the expansion joint 1006 in the third socket 522 of the single rod 508, as indicated by a double sided arrow 1106. Further, during heating of the emitter 424 to emit electrons and generate X-ray beams, the emitter 424 may thermally expand. Thermal expansion of the emitter 424 may further be translated into axial movement of the expansion joint 1006 in the third socket 522 of the single rod 508, as indicated by the double sided arrow 1106.

FIG. 12 shows a third example of the compliant, single rod insulator assembly 1202, comprising a pin joint 1204 configured to allow axial motion of the emitter 424 and apply rigid radial support to the emitter 424. The third example of the compliant, single rod insulator assembly 1202 may be implemented in the second example emitter assembly 1002, where a top surface 506 of the pin joint 1204 is fixedly coupled to the emitter 424. The pin joint 1204 is positioned in the third socket 522 of the single rod 508. In the third example of the compliant, single rod insulator assembly 1202, the third socket 522 has a rectangular shape configured to receive a planar, rectangular shape of the pin joint 1204. The pin joint 1204 is positioned in the third socket 522, and a pin 1206 extends through the pin joint 1204 and the single rod 508 to couple the pin joint 1204 to the single rod 508. The pin 1206 is positioned perpendicular to the axial direction (e.g., the pin 1206 is positioned along the z-axis). The pin 1206 may act as a hinge and/or a pivot point at which the pin joint 1204 may move axially, relative to the single rod 508. The pin joint 1204 may further apply rigid radial support to the emitter 424. For example, in response to the X-ray tube in which the emitter assembly is positioned (e.g., the X-ray tube 300 of FIG. 3) being rotated during an imaging operation, the emitter 424 may experience centrifugal forces. The two-rod insulator assembly 412, described with respect to FIGS. 4-10, fixedly positions the emitter 424 in the cathode cup 362 at the first end 426 of the emitter 424. The third example of the compliant, single rod insulator assembly 1202 transmits centrifugal forces on the emitter 424 into axial movement of the pin joint 1204 in the third socket 522 of the single rod 508, as indicated by a double sided arrow 1208. For example, the pin joint 1204 may move in an arched curve with a range of motion of the curve controlled by the pin joint 1204 contacting the single rod 508. Further, during heating of the emitter 424 to emit electrons and generate X-ray beams, the emitter 424 may thermally expand. Thermal expansion of the emitter 424 may further be translated into axial movement of the pin joint 1204 in the third socket 522 of the single rod 508, as indicated by the double sided arrow 1208.

FIG. 13 shows a fourth example of the compliant, single rod insulator assembly 1302, wherein the single rod 508 is configured as an I-beam support rod. The I-beam support rod provides radial support that may be multiple orders of magnitude greater than axial support due to the I-beam cross section. The emitter 424 may be fixedly coupled to a top surface 506 of the single rod 508, and movement/thermal expansion of the emitter 424 may be translated into axial movement of the single rod 508, such as material deformation including a bend or a curve in a center region 1304 of the I-beam.

In this way, an emitter assembly is provided for an X-ray beam that comprises an emitter with a fixed support at a first end and compliant support at a second end, opposite the first end. The compliant mechanism provides both fixed and unfixed degrees of freedom, which enables thermal expansion and movement of the emitter. This may reduce shorting due to compression, such as may occur in fixed emitters (e.g., fixed in six degrees of freedom from the first end and the second end) due to thermal expansion of the emitter and/or G force/centrifugal forces experienced by the emitter.

The emitter assembly enables movement and/or thermal expansion of an emitter via a fixed/rigid support of the emitter at a first end by a two-rod insulator assembly, and via compliant support of the emitter at a second end by a compliant, single rod insulator assembly. The fixed/rigid support and the compliant support may desirably position the emitter in the cathode cup. During operation of the X-ray beam, which may include rotation of the X-ray beam and heating of the emitter, compression of the emitter and possible shorting of the emitter due to compression may be mitigated, as centrifugal forces and thermal expansion of the emitter may be directed to axial movement of the emitter via the compliant support. The cathode may thus have increased reliability and X-ray beam emission performance. The technical effect of a cathode for an imaging system as described herein is increased electron focusing ability of the cathode, high-voltage stability of the cathode, and increased yield of manufactured cathodes.

The disclosure also provides support for an X-ray emitter assembly, comprising: a first end of a substantially flat emitter supported by two rods extending from a two-rod insulator assembly, and a second end of the substantially flat emitter supported by a compliant, single rod insulator assembly. In a first example of the system, the compliant, single rod insulator assembly comprises a single rod extending from an insulator. In a second example of the system, optionally including the first example, the compliant, single rod insulator assembly further comprises a substantially flat support plate comprising a socket, where the substantially flat emitter is inserted into the socket and the substantially flat support plate is perpendicular to the substantially flat emitter. In a third example of the system, optionally including one or both of the first and second examples, the single rod is welded to the substantially flat support plate. In a fourth example of the system, optionally including one or more or each of the first through third examples, the substantially flat emitter is welded to the substantially flat support plate at the socket. In a fifth example of the system, optionally including one or more or each of the first through fourth examples, the single rod comprises a socket, and the compliant, single rod insulator assembly further comprises an expansion joint where the expansion joint is inserted into the socket of the single rod, and the expansion joint is coupled to the substantially flat emitter. In a sixth example of the system, optionally including one or more or each of the first through fifth examples, the single rod is configured to apply rigid radial support to the substantially flat emitter and enable axial movement of the substantially flat emitter.

The disclosure also provides support for a substantially flat emitter, comprising: a first end supported by at least one rod extending from an insulator assembly, and a second end supported by a substantially flat support plate comprising a socket, where the second end is inserted into the socket and the substantially flat support plate is perpendicular to a planar emission surface. In a first example of the system, the socket of the substantially flat support plate has a length configured to accommodate a thermal expansion of the substantially flat emitter. In a second example of the system, optionally including the first example, the substantially flat support plate further comprises a second socket configured to support a second emitter positioned parallel to the substantially flat emitter. In a third example of the system, optionally including one or both of the first and second examples, the substantially flat support plate is mounted on a single rod extending from an insulator. In a fourth example of the system, optionally including one or more or each of the first through third examples, the single rod is coupled to the substantially flat support plate via a weld. In a fifth example of the system, optionally including one or more or each of the first through fourth examples, the substantially flat emitter is a two-pass ribbon emitter. In a sixth example of the system, optionally including one or more or each of the first through fifth examples, the insulator assembly is a two-rod insulator assembly with a first rod and a second rod extending therefrom, and where the first rod and the second rod are fixedly coupled to the substantially flat emitter at the first end. In a seventh example of the system, optionally including one or more or each of the first through sixth examples, a top surface of each of the first rod and the second rod are coplanar. In an eighth example of the system, optionally including one or more or each of the first through seventh examples, the substantially flat emitter is a single pass emitter.

The disclosure also provides support for an X-ray tube, comprising: an anode, a cathode, a cathode cup of the cathode, and an emitter positioned in the cathode cup, the emitter comprising a first end supported by two rods extending from a two-rod insulator assembly, and a second end supported by a compliant, single rod insulator assembly. In a first example of the system, the system further comprises: one or more additional emitters positioned parallel to the emitter and supported by the two-rod insulator assembly and by the compliant, single rod insulator assembly. In a second example of the system, optionally including the first example, the two-rod insulator assembly is brazed into the cathode cup. In a third example of the system, optionally including one or both of the first and second examples, the cathode cup comprises a channel in which the compliant, single rod insulator assembly is positioned, where a single rod of the compliant, single rod insulator assembly is configured to apply rigid radial support to the emitter and enable axial movement of the emitter.

FIGS. 3-13 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray emitter assembly, comprising:
a first end of a substantially flat emitter supported by two rods extending from a two-rod insulator assembly; and
a second end of the substantially flat emitter supported by a compliant, single rod insulator assembly, wherein the compliant, single rod insulator assembly comprises a single rod extending from an insulator.

2. The X-ray emitter assembly of claim 1, wherein the compliant, single rod insulator assembly further comprises a substantially flat support plate comprising a socket, where the substantially flat emitter is inserted into the socket and the substantially flat support plate is perpendicular to the substantially flat emitter.

3. The X-ray emitter assembly of claim 2, wherein the single rod is welded to the substantially flat support plate.

4. The X-ray emitter assembly of claim 2, wherein the substantially flat emitter is welded to the substantially flat support plate at the socket.

5. The X-ray emitter assembly of claim 1, wherein the single rod comprises a socket, and the compliant, single rod insulator assembly further comprises an expansion joint where the expansion joint is inserted into the socket of the single rod, and the expansion joint is coupled to the substantially flat emitter.

6. The X-ray emitter assembly of claim 1, wherein the single rod is configured to apply rigid radial support to the substantially flat emitter and enable axial movement of the substantially flat emitter.

7. A substantially flat emitter, comprising:

a first end supported by at least one rod extending from an insulator assembly; and a second end supported by a substantially flat support plate comprising a socket, where the second end is inserted into the socket and the substantially flat support plate is perpendicular to a planar emission surface, wherein the substantially flat support plate further comprises a second socket configured to support a second emitter positioned parallel to the substantially flat emitter.

8. The substantially flat emitter of claim 7, wherein the socket of the substantially flat support plate has a length configured to accommodate a thermal expansion of the substantially flat emitter.

9. The substantially flat emitter of claim 7, wherein the substantially flat support plate is mounted on a single rod extending from an insulator.

10. The substantially flat emitter of claim 9, wherein the single rod is coupled to the substantially flat support plate via a weld.

11. The substantially flat emitter of claim 7, wherein the substantially flat emitter is a two-pass ribbon emitter.

12. The substantially flat emitter of claim 11, wherein the insulator assembly is a two-rod insulator assembly with a first rod and a second rod extending therefrom, and where the first rod and the second rod are fixedly coupled to the substantially flat emitter at the first end.

13. The substantially flat emitter of claim 12, wherein a top surface of each of the first rod and the second rod are coplanar.

14. The substantially flat emitter of claim 7, wherein the substantially flat emitter is a single pass emitter.

15. An X-ray tube, comprising:

an anode;

a cathode;

a cathode cup of the cathode; and an emitter positioned in the cathode cup, the emitter comprising a first end supported by two rods extending from a two-rod insulator assembly, and a second end of the emitter that is opposite the first end is supported by a single rod of a compliant, single rod insulator assembly.

16. The X-ray tube of claim 15, further comprising one or more additional emitters positioned parallel to the emitter and supported by the two-rod insulator assembly and by the compliant, single rod insulator assembly.

17. The X-ray tube of claim 15, wherein the two-rod insulator assembly is brazed into the cathode cup.

18. The X-ray tube of claim 15, wherein the cathode cup comprises a channel in which the compliant, single rod insulator assembly is positioned, where the single rod of the compliant, single rod insulator assembly is configured to apply rigid radial support to the emitter and enable axial movement of the emitter.

19. The X-ray tube of claim 15, wherein the compliant, single rod insulator assembly comprises only one rod.

20. The X-ray tube of claim 15, wherein the two-rod insulator assembly comprises only two rods.

* * * * *